United States Patent
Borza et al.

(10) Patent No.: US 11,026,946 B2
(45) Date of Patent: Jun. 8, 2021

(54) PHARMACOLOGICALLY ACTIVE ALICYCLIC-SUBSTITUTED PYRAZOLO[1,5-A]PYRIMIDINE DERIVATIVES

(71) Applicant: RICHTER GEDEON NYRT., Budapest (HU)

(72) Inventors: István Borza, Budapest (HU); Viktor Román, Érd (HU); János Éles, Budapest (HU); Zsuzsa Hadady, Debrecen (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 16/493,453

(22) PCT Filed: Mar. 12, 2018

(86) PCT No.: PCT/IB2018/051599
§ 371 (c)(1),
(2) Date: Sep. 12, 2019

(87) PCT Pub. No.: WO2018/167630
PCT Pub. Date: Sep. 20, 2018

(65) Prior Publication Data
US 2020/0129515 A1    Apr. 30, 2020

(30) Foreign Application Priority Data
Mar. 13, 2017    (HU) .................................. P1700108

(51) Int. Cl.
| | | |
|---|---|---|
| A61P 25/28 | (2006.01) | |
| C07D 487/04 | (2006.01) | |
| A61K 31/519 | (2006.01) | |
| A61K 45/06 | (2006.01) | |
| C07D 491/147 | (2006.01) | |

(52) U.S. Cl.
CPC ............ *A61K 31/519* (2013.01); *A61K 45/06* (2013.01); *A61P 25/28* (2018.01); *C07D 487/04* (2013.01); *C07D 491/147* (2013.01)

(58) Field of Classification Search
CPC .................................................. C07D 487/04
See application file for complete search history.

(56) References Cited

U.S. PATENT DOCUMENTS
2016/0304527 A1    10/2016  Faghih et al.

FOREIGN PATENT DOCUMENTS
| | | |
|---|---|---|
| WO | WO 2005/094828 | 10/2005 |
| WO | WO 2006/136442 | 12/2006 |
| WO | WO 2007/139240 | 12/2007 |
| WO | WO 2009/123986 | 10/2009 |
| WO | WO 2015/056771 | 4/2015 |
| WO | WO 2017/069270 | 4/2017 |
| WO | WO 2018/167629 | 9/2018 |

OTHER PUBLICATIONS

Stella (J. Pharmaceutical Sciences, 2010, 99(12), pp. 4755-4765).*
Bettler, B., et al., "Molecular Structure and Physiological Functions of $GABA_B$ Receptors," *Physiol. Rev.* 84:835-867, 2004, American Physiological Society, United States.
Biermann, B., et al., "The Sushi Domains of $GABA_B$ Receptors Function as Axonal Targeting Signals," *J. Neurosci.* 30(4):1385-1394, 2010, Society for Neuroscience, United States.
Binet, V., et al., "The Heptahelical Domain of $GABA_{B2}$ is Activated Directly by CGP7930, a Positive Allosteric Modulator of the $GABA_B$ Receptor," *J. Biol. Chem.* 279(28):29085-29091, 2004, American Society for Biochemistry and Molecular Biology, Inc., United States.
Bowery, N.G., et al., "$GABA_A$ and $GABA_B$ Receptor Site Distribution in the Rat Central Nervous System," *Neuroscience* 20(2):365-383, 1987, Pergamon Journals Ltd., England.
Breslow, M.F., et al., "Role of γ-Aminobutyric Acid in Antipanic Drug Efficacy," *Am. J. Psychiatry* 146(3):353-356, 1989, American Psychiatric Association, United States.

(Continued)

*Primary Examiner* — Susanna Moore
(74) *Attorney, Agent, or Firm* — Sterne, Kessler, Goldstein & Fox P.L.L.C.

(57) ABSTRACT

The present invention relates to new pyrazolo[1,5-a]pyrimidine derivatives of formula (I) or pharmaceutically acceptable salts, biologically active metabolites, pro-drugs, racemates, enantiomers, diastereomers, solvates and hydrates thereof that serve as GABAB receptor positive allosteric modulators. The invention al so relates to the process for producing such compounds. The invention further relates to pharmaceutical compositions comprising such compounds optionally in combination with two or more different therapeutic agents and the use of such compounds in methods for treating diseases and conditions mediated and modulated by the GABAB receptor positive allosteric mechanism. The invention al so provides a method for manufacture of medicaments useful in the treatment of such disorders.

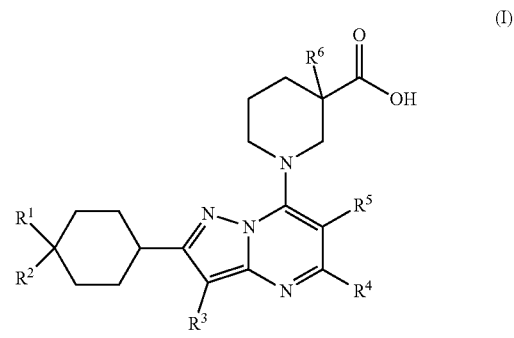

24 Claims, No Drawings

(56) References Cited

OTHER PUBLICATIONS

Chalifoux, J.R., et al., "GABA$_B$ receptor modulation of synaptic function," Curr. Opin. Neurobiology 21:339-344, 2011, Elsevier, United States.
Conn, P.J., et al., "Allosteric modulators of GPCRs: a novel approach for the treatment of CNS disorders," Nat. Reviews 8:41-54, 2009, Macmillan Publishers Limited, Germany.
Cryan, J.F., et al., "Behavioral Characterization of the Novel GABA$_B$ Receptor-Positive Modulator GS39783 (N,N'-Dicyclopentyl-2-methylsulfanyl-5-nitro-pyrimidine-4,6-diamine): Anxiolytic-Like Activity without Side Effects Associated with Baclofen or Benzodiazepines," J. Pharmacol. Exp. Therap. 310(3):952-963, 2004, American Society for Pharmacology and Experimental Therapeutics, United States.
Drake, R.G., et al., "Baclofen Treatment for Chronic Posttraumatic Stress Disorder," Annals of Pharmacother. 37:1177-1181, 2003, Harvey Whitney Books Company, United States.
Dupuis, D.S., et al., "Point Mutations in the Transmembrane Region of GABA$_{B2}$ Facilitate Activation by the Positive Modulator N,N'-Dicyclopentyl-2-methylsulfanyl-5-nitro-pyrimidine-4,6-diamine (GS39783) in the Absence of the GABA$_{B2}$ Subunit," Mol. Pharmacol. 70(6):2027-2036, 2006, American Society for Pharmacology and Experimental Therapeutics, United States.
Gassmann, M., et al., "Redistribution of GABA$_{B(1)}$ Protein and Atypical GABA$_B$ Responses in GABA$_{B(2)}$-Deficient Mice," J. Neurosci. 24(27):6086-6097, 2004, Society for Neuroscience, United States.
Gjoni, T., et al., "Receptor activation involving positive allosteric modulation, unlike full agonism, does not result in GABA$_B$ receptor desensitization," Neuropharmacol. 55:1293-1299, 2008, Elsevier, United States.
Hill, D.R., et al., "$^3$H-baclofen and $^3$H-GABA bind to bicuculline-insensitive GABA$_B$ sites in rat brain," Nature 290:149-152, 1981, Macmillan Journals Ltd., Germany.
Keegan, B.M.T., et al., "Chronic baclofen desensitizes GABA$_B$-mediated G-protein activation and stimulates phosphorylation of kinases in mesocorticolimbic rat brain," Neuropharmacol. 95:492-502, 2015, Elsevier, United States.
Leggio, L., et al., "Effectiveness and Safety of Baclofen in the Treatment Dependent Patients," CNS & Neurol. Disord—Drug Targ. 9:33-44, 2010, Bentham Science Publishers Ltd., United States.
Mombereau, C., et al., "Genetic and Pharmacological Evidence of a Role for GABA$_B$ Receptors in the Modulation of Anxiety- and Antidepressant-Like Behavior," Neuropsychopharmacol. 29:1050-1062, 2004, Nature Publishing Group, United States.
Mombereau, C., et al., "Altered response to benzodiazepine anxiolytics in mice lacking GABA$_{B(1)}$ receptors," Eur. J. Pharmacol. 496:119-120, 2004, Elsevier, United States.
Mombereau, C., et al., "Altered anxiety and depression-related behavior in mice lacking GABA$_{B(2)}$ receptor subunits," NeuroReport 16:307-310, 2005, Lippincott Williams & Wilkins, United States.
Ross, J.C., et al., "Acute Intrathecal Baclofen Withdrawal: A Brief Review of Treatment Options," Neurocrit. Care 14:103-108, 2011, Neurocritical Care Society, United States.
Schuler, V.S., et al., "Epilepsy, Hyperalgesia, Impaired Memory, and Loss of Pre- and Postsynaptic GABA$_B$ Responses in Mice Lacking GABA$_{B(1)}$," Neuron 31:47-58, 2001, Cell Press, United States.
Ulrich, D., et al., "GABA$_B$ receptors: synaptic functions and mechanisms of diversity," Curr. Opin. Neurobiol. 17:298-303, 2007, Elsevier, United States.
Vacher, C.-M., et al., "GABA$_B$ Receptors as Potential Therapeutic Agents," Curr. Drug Targets—CNS & Neurol. Disord. 2:251-263, 2003, Bentham Science Publishers Ltd., United States.
Vigot, R., et al., "Differential Compartmentalization and Distinct Functions of GABA$_B$ Receptor Variants," Neuron 50:589-601, 2006, Elsevier, United States.
Wang, L., et al., "Allosteric Modulators of G Protein-Couples Receptors: Future Therapeutics for Complex Physiological Disorders," J. Pharmacol. Exper. Therap. 331(2):340-348, 2009, American Society for Pharmacology and Experimental Therapeutics, United States.
A Study to Evaluate the Efficacy and Safety of Arbaclofen Placarbil (XP19986) as Adjunctive Therapy in Subjects With Gastroesophageal Reflux Disease (GERD), NCT00978016, ClinicalTrials.gov, accessed at https://clinicaltrials.gov/ct2/show/NCT00978016, accessed on Jan. 22, 2021, 7 pages.
Arbaclofen in Children and Adolescents With ASD (AIMS2-CT1), NCT03682978, ClinicalTrials.gov, accessed at https://clinicaltrials.gov/ct2/show/NCT03682978, accessed on Jan. 22, 2021, 15 pages.
Arbaclofen vs. Placebo in the Treatment of Children and Adolescents With ASD (ARBA) (ARBA), NCT03887676, ClinicalTrials.gov, accessed at https://clinicaltrials.gov/ct2/show/NCT03887676, accessed on Jan. 22, 2021, 8 pages.
Arima H, Oiso Y "Positive effect of baclofen on body weight reduction in obese subjects: a pilot study." Intern. Med. 49:2043-2047. John Wiley & Sons, Inc., United States (2010).
Auteri M, et al. "GABA and GABA receptors in the gastrointestinal tract: from motility to inflammation." Pharmacol. Res. 93:11-21, Elsevier, Netherlands (2015).
Benke B., "GABAB Receptors and Pain." Curr. Top. Behav. Neurosci. 27 pages, Springer Nature, Switzerland (2020).
Bettler, Bernhard, et al. "Molecular structure and physiological functions of GABAB receptors." Physiological reviews 84(3): 835-867, The American Physiological Society (2004).
Blok, B. F. M., and G. Holstege. "The central control of micturition and continence: implications for urology." BJU international 83(S2): 1-6, John Wiley & Sons, United States (1999).
Boeckxstaens GE, et al. "Effect of lesogaberan, a novel GABA(B)-receptor agonist, on transient lower oesophageal sphincter relaxations in male subjects." Aliment. Pharmacol. Ther. 31:1208-1217, Wiley-Blackwell, United States (2010).
Brändén L, et al. "The novel, peripherally restricted GABAB receptor agonist lesogaberan (AZD3355) inhibits acid reflux and reduces esophageal acid exposure as measured with 24-h pHmetry in dogs." Eur. J. Pharmacol. 634:138-141, Elsevier, Netherlands (2010).
Broft AI, et al. "Baclofen for binge eating: an open-label trial." Int. J. Eat. Disord. 40:687-691, John Wiley & Sons, Inc., United States (2007).
Brusberg M, "The GABA(B) receptor agonist, baclofen, and the positive allosteric modulator, CGP7930, inhibit visceral pain-related responses to colorectal distension in rats." Neuropharmacology 56:362-367. Elsevier, Netherlands (2009).
Canning BJ, et al. "Antitussive effects of the peripherally restricted GABAB receptor agonist lesogaberan in guinea pigs: comparison to baclofen and other GABAB receptor-selective agonists." Cough 8:7, pp. 1-7 Biomed Central, England (2012).
Castelli, M. Paola, et al. "Distribution of GABAB receptor mRNAs in the rat brain and peripheral organs." Life sciences 64(15): 1321-1328, Elsevier, Netherlands (1999).
Corwin RL, et al. "Baclofen reduces binge eating in a double-blind, placebo-controlled, crossover study." Behav. Pharmacol. 23:616-625, Lippincott, United States (2012).
Ebenezer IS, Patel, "Effects of intraperitoneal administration of the GABAB receptor agonist baclofen on food intake in rats measured under different feeding conditions." Eur. J. Pharmacol. 653:58-62, Elsevier, Netherlands (2011).
Erickson CA, et al. "STX209 (Arbaclofen) for Autism Spectrum Disorders: An 8-Week Open-Label Study." J. Aut. Dev. Disord. 44:958-964, Springer Publishing, Germany (2014).
Fatemi SH, et al. "Expression of GABA(B) receptors is altered in brains of subjects with autism." Cerebellum 8:64-69, Springer Science+Business Media, Germany (2009).
Featherstone RE, et al. "Baclofen restores excitatory-inhibitory balance in 15q13.3 deletion mice." Biol. Psychiatry 77: 9 Suppl. 1 (399S), Elsevier, Netherlands (2015).
Fontenelle LF et al., "Obsessive-compulsive disorder, impulse control disorders and drug addiction: common features and potential treatments." Drugs 71:827-840, Springer Publishing, Germany (2011).
Frye RE, "Clinical potential, safety, and tolerability of arbaclofen in the treatment of autism spectrum disorder." Drug Healthc. Patient Saf. 6:69-76, Dove Medical Press, England (2014).

(56) References Cited

OTHER PUBLICATIONS

Gerson LB, et al. "Arbaclofen placarbil decreases postprandial reflux in patients with gastroesophageal reflux disease." Am. J. Gastroenterol. 105:1266-1275, Lippincott Williams & Wilkins, United States (2010).
Gogolla N, et al. "Common circuit defect of excitatory-inhibitory balance in mouse models of autism" J. Neurodev. Disord. 1:172-181, Biomed Central, England (2009).
Hamad, Mousa, et al. "Potential for intrathecal baclofen in treatment of essential tremor." World neurosurgery 105: 170-175, Elsevier, Netherlands (2017).
Haubensak, K. "A Double-Blind Trial with the Antispasticity Drug Lioresal® in 15 Paraplegics with Upper Neuron Lesions." Urologia internationalis 32(2-3): 198-201, Karger Publishers, Switzerland (1977).
Healy A, et al. "Fragile X Syndrome: An Update on Developing Treatment Modalities." ACS Chem. Neurosci. 2:402-410, American Chemical Society (2011).
Henderson C, et al. "Reversal of disease-related pathologies in the fragile X mouse model by selective activation of GABAB receptors with arbaclofen." Sci. Transl. Med. 4:116-126, American Association for the Advancement of Science (2012).
Hyland NP, Cryan JF "A gut feeling about GABA: focus on GABAB receptors." Front. Pharonacol. 1:124, 1-9 Frontiers Media, Switzerland (2010).
Igawa, Yasuhiko, et al., "Effects of GABA-receptor stimulation and blockade on micturition in normal rats and rats with bladder outflow obstruction." The Journal of urology 150(2): 537-542, American Urological Association, Inc (1993).
Investigate the Effect of Different Doses of Lesogaberan (AZD3355) as add-on to PPI in GERD Patients With Partial Response to PPI, NCT01005251, ClinicalTrials.gov, accessed at https://clinicaltrials.gov/ct2/showNCT01005251, accessed on Jan. 22, 2021, 7 pages.
Kalinichev M, et al., "Evaluation of peripheral versus central effects of GABAB receptor activation using a novel, positive allosteric modulator of the GABAB receptor ADX71943, a pharmacological tool compound with a fully peripheral activity profile." Br. J. Pharmacol. 171:4941-4954, Wiley-Blackwell, United States (2014).
Kalinichev M, et al., "The drug candidate, ADX71441, is a novel, potent and selective positive allosteric modulator of the GABAB receptor with a potential for treatment of anxiety, pain and spasticity." Neuropharmacology 114:34-47, Elsevier, Netherlands (2017).
Kang JY et al., "Deficits in the activity of presynaptic γ-aminobutyric acid type B receptors contribute to altered neuronal excitability in fragile X syndrome." J. Biol. Chem. 292:6621-6632, American Society for Biochemistry and Molecular Biology (2017).
Lee E, Lee J, Kim E "Excitation/Inhibition Imbalance in Animal Models of Autism Spectrum Disorders." Biol Psychiatry 81(10):838-847, Society of Biological Psychiatry (2017).
Li S, et al. "The effects of baclofen for the treatment of gastroesophageal reflux disease: a meta-analysis of randomized controlled trials." Gastroenterol. Res. Pract. 2014:307805, 1-8, Hindawi Publishing, England (2014).
Lu Y, Westlund KN "Effects of baclofen on colon inflammation-induced Fos, CGRP and SP expression in spinal cord and brainstem." Brain Res. 889:118-130, Elsevier, Netherlands (2001).
Mabunga DF et al., "Exploring the Validity of Valproic Acid Animal Model of Autism." Exp. Neurobiol. 24:285-300, Nencki Institute of Experimental Biology and the Polish Neuroscience Society (2015).
Miner PB Jr, et al. "Dose-dependent effects of lesogaberan on reflux measures in patients with refractory gastroesophageal reflux disease: a randomized, placebo-controlled study." BMC Gastroenterol. 14:188, 1-12, BioMed Central Ltd., England (2014).
Miyazato, Minoru, et al. "GABA receptor activation in the lumbosacral spinal cord reduces detrusor overactivity in spinal cord injured rats." The Journal of urology 179(3):1178-1183, Elsevier, Netherlands (2008).
Nicolini C, Fahnestock M, "The valproic acid-induced rodent model of autism." Exp Neurol 299(Pt A):217-227, Elsevier, Netherlands (2018).

Oblak A, et al. "Decreased GABAA receptors and benzodiazepine binding sites in the anterior cingulate cortex in autism." Autism Res. 2:205-219, Wiley-Blackwell, United States (2009).
Open-Label study of the safety and tolerability of STX209 in subjects with autism spectrum disorders, NCT0846547, ClinicalTrials.gov, accessed at https://clinicaltrials.gov/ct2/show/ NCT0846547, accessed on Jan. 22, 2021, 7 pages.
Pacey LKK, et al., "Subchronic administration and combination metabotropic glutamate and GABAB receptor drug therapy in fragile X syndrome." J. Pharmacol. Exp. Ther. 338:897-905, (2011).
Palea, Stefano, et al. "Comparison of the effects of netupitant and tolterodine on overactive bladder induced by intravesical acetic acid infusion in anesthetized female guinea-pigs." Neurourol Urodyn 29: 994-995, John Wiley & Sons, United States (2010).
Paris-Robidas, Sarah, et al. "Defective dentate nucleus GABA receptors in essential tremor." Brain 135(1): 105-116, Oxford University Press, England (2012).
Patel SM, Ebenezer IS, "Effects of chronic systemic administration of the GABA(B) receptor agonist baclofen on food intake and body weight in rats." Eur. J. Pharmacol, Elsevier, Netherlands 635:129-134. (2010).
Paterson, Neil E., et al. "Pharmacological characterization of harmaline-induced tremor activity in mice." European journal of pharmacology 616(1-3): 73-80, Elsevier, Netherlands (2009).
Phirson, Rikard, Anders Lehmann, and Karl-Erik Andersson. "Effects of γ-aminobutyrate B receptor modulation on normal micturition and oxyhemoglobin induced detrusor overactivity in female rats." The Journal of urology 168(6): 2700-2705, American Urological Association (2002).
Pelsőczi P, et al. "Disrupted Social Hierarchy in Prenatally Valproate-Exposed Autistic-Like Rats." Front Behav Neurosci 13:295, 1-12, Frontiers Media, Switzerland (2020).
Perdona E, et al. "In vitro and in vivo characterization of the novel GABAB receptor positive allosteric modulator, 2-{1-[2-(4-chlorophenyl)-5-methylpyrazolo[1,5-a]pyrimidin-7-yl]-2-piperidinyl}eethanol (CMPPE)." Neuropharmacology 61:957-966, Elsevier, Netherlands (2011).
Qin M, et al. "R-Baclofen Reverses a Social Behavior Deficit and Elevated Protein Synthesis in a Mouse Model of Fragile X Syndrome." Int. J. Neuropsychopharmacol. 18(9): 1-13, Nature Research, England (2015).
Safety, Tolerability and Efficacy Study of STX209 in Subjects With Fragile X Syndrome, NCT00788073, ClinicalTrials.gov, accessed at https://clinicaltrials.gov/ct2/show/NCT00788073, accessed on Jan. 22, 2021, 7 pages.
Safety, Tolerability, and Efficacy of Arbaclofen in 16p11.2 Deletion, NCT04271332, ClinicalTrials.gov, accessed at https://clinicaltrials.gov/ct2/show/ NCT04271332, accessed on Jan. 28, 2021, 8 pages.
Sanger, G. J., et al. "GABAB receptor function in the ileum and urinary bladder of wildtype and GABAB1 subunit null mice." Autonomic and Autacoid Pharmacology 22.3: 147-154, Blackwell Publishing Ltd (2002).
Shaheen NJ, et al. "Efficacy and safety of lesogaberan in gastro-oesophageal reflux disease: a randomised controlled trial." Gut 62:1248-1255, BMJ Publishing, England (2013).
Shanker, Vicki. "Essential tremor: diagnosis and management." BMJ 366, 1-16, British Medical Association, England (2019).
Silverman JL, et al. "GABAB Receptor Agonist R-Baclofen Reverses Social Deficits and Reduces Repetitive Behavior in Two Mouse Models of Autism." Neuropsychopharmacology 40:2228-2239, Nature Research, England (2015).
Sinclair D, et al. "GABA-B Agonist Baclofen Normalizes Auditory-Evoked Neural Oscillations and Behavioral Deficits in the Fmr1 Knockout Mouse Model of Fragile X Syndrome." eNeuro. 4(1):1-13, Society for Neuroscience, United States (2017).
Sohal VS, Rubenstein, "Excitation-inhibition Balance as a Framework for Investigating Mechanisms in Neuropsychiatric Disorders." Mol Psychiatry 24(9):1248-1257, Nature Research, England (2019).
Spisák T, et al. "Purkinje cell number-correlated cerebrocerebellar circuit anomaly in the valproate model of autism." Sci Rep. 9(1):9225, 1-15, Nature Research, England (2019).
Study of Arbaclofen for the Treatment of Social Withdrawal in Subjects With Autism Spectrum Disorders, NCT01288716, ClinicalTri-

(56) References Cited

OTHER PUBLICATIONS als.gov, accessed at https://clinicaltrials.gov/ct2/show/ NCT01288716, accessed on Jan. 28, 2021, 5 pages.

Tariq, Mohammad, et al. "Baclofen attenuates harmaline induced tremors in rats." Neuroscience letters 312(2): 79-82, Elsevier, Netherlands (2001).

Taylor, M. C., and C. P. Bates. "A double-blind crossover trial of baclofen—a new treatment for the unstable bladder syndrome." British Journal of Urology 51(6): 504-505. British Association of Urological Surgeons (1979).

Vakil NB, et al., "Randomised clinical trial: arbaclofen placarbil in gastro-oesophageal reflux disease—insights into study design for transient lower sphincter relaxation inhibitors." Aliment. Pharmacol. Ther. 38(2):107-117, Wiley-Blackwell, United States (2013).

Veenstra-Vanderweele J, et al. "Arbaclofen in Children and Adolescents with Autism Spectrum Disorder: A Randomized, Controlled, Phase 2 Trial." Neuropsychopharmacology 42:1390-1398, Nature Research, England (2017).

Von Deneen KM, Liu Y, "Obesity as an addiction: Why do the obese eat more?" Maturitas 68:342-345, Elsevier, Netherlands (2011).

Wojnicki FHE, et al., "Effects of baclofen on operant performance for food pellets and vegetable shortening after a history of binge-type behavior in non-food deprived rats." Pharmacol. Biochem. Behav. 84:197-206, Elsevier, Netherlands (2006).

Xu, Danfeng, et al. "Dysfunctional voiding confirmed by transdermal perineal electromyography, and its effective treatment with baclofen in women with lower urinary tract symptoms: a randomized double-blind placebo-controlled crossover trial." BJU international 100(3): 588-592, Wiley-Blackwell, United States (2007).

Zhang W, et al., "GABAB receptor upregulates fragile X mental retardation protein expression in neurons." Sci. Rep. 5:10468, 1-13, Nature Publishing, England (2015).

Lord, Catherine, et al., "Autism spectrum disorder." Nature Reviews Disease Primers 6:5, pp. 1-25, Springer Nature Publishing, United States (2020).

\* cited by examiner

PHARMACOLOGICALLY ACTIVE ALICYCLIC-SUBSTITUTED PYRAZOLO[1,5-A]PYRIMIDINE DERIVATIVES

FIELD OF THE INVENTION

The present invention relates to new pyrazolo[1,5-a]pyrimidine derivatives of formula (I) or pharmaceutically acceptable salts, biologically active metabolites, pro-drugs, racemates, enantiomers, diastereomers, solvates and hydrates thereof that serve as $GABA_B$ receptor positive allosteric modulators. The invention also relates to the process for producing such compounds. The invention further relates to pharmaceutical compositions comprising such compounds optionally in combination with two or more different therapeutic agents and the use of such compounds in methods for treating diseases and conditions mediated and modulated by the $GABA_B$ receptor positive allosteric mechanism. The invention also provides a method for manufacture of medicaments useful in the treatment of such disorders.

BACKGROUND OF THE INVENTION

Gamma-aminobutyric acid (GABA) is the main inhibitory neurotransmitter in the central nervous system and plays a key role in modulating neuronal activity. It exerts its action via three receptor systems, the related ionotropic $GABA_A$ and $GABA_C$ receptors, and the distinct metabotropic $GABA_B$ receptors (Hill and Bowery, Nature 1981, 290, 149-152). The latter $GABA_B$ receptors are widespreadly distributed within the mammalian central nervous system with various expression levels in different brain regions (Bovery et al, Neuroscience 1987, 20, 365-385). $GABA_B$ receptors can be found both pre- and postsynaptically and play an important role in the fine-tuning of neurotransmission. Most $GABA_B$ receptors cluster around excitatory synapses, either at the edge of the presynaptic terminal or on dendritic spines opposite to glutamatergic boutons (Ulrich and Bettler, Curr. Opin. Neurobiol. 2007, 17, 298-303).

$GABA_B$ receptors belong to the Family 3 (C) of G-protein coupled receptors (GPCRs) together with metabotropic glutamate receptors (mGluRs), calcium-sensing receptors, taste receptors and a number of orphan receptors, showing highest, approximately 30% homology to mGluRs (Bettler et al, Physiol. Rev. 2004, 84, 835-867). $GABA_B$ receptors are heterodimers consisting of two similar, yet different subunits, B1 and B2. The B1 subunit has multiple splice variants with only two (B1a and B1b) having clear physiological significance. These isoforms differ only in their extracellular domain containing two Sushi motifs that regulate the subcellular localization of the receptor (Vigot et al, Neuron 2006, 50, 589-601; Biermann et al, J. Neurosci. 2010, 30, 1385-1394). The B1 subunit binds the endogenous neurotransmitter ligand GABA as well as other orthosteric agonists (such as baclofen, SKF97541) and antagonists (such as phaclofen, saclofen). The B2 subunit is responsible for G-protein activation-mediated intracellular signal transduction and is believed to bind allosteric modulators (Binet et al, J. Biol. Chem. 2004, 279, 29085-29091; Dupuis et al, Mol. Pharmacol. 2006, 70, 2027-2036). The site of action for the Novartis $GABA_B$ positive allosteric modulator compounds CGP7930 and GS39783 is the heptahelical transmembrane domain of the B2 subunit; the exact binding site for other, unrelated positive allosteric modulator chemotypes is not known.

The main synaptic effects of $GABA_B$ receptors are the presynaptic blockade of neurotransmitter release (GABA as well as glutamate) and postsynaptic hyperpolarization (Gassmann and Bettler, in Handbook of Contemporary Neuropharmacology 2007). These effects are the result of inhibition of presynaptic calcium influx and stimulation of postsynaptic inwardly rectifying potassium (GIRK) channels, respectively. Ion channel functions are mediated in a membrane-delimited manner through the activation of βγ subunits of $G_i/G_o$ proteins. In addition to these, $GABA_B$ receptors also signal via the a subunit of the same G-proteins that inhibits adenylate cyclase and retards the recruitment of synaptic vesicles (Chalifoux and Carter, Curr. Opin. Neurobiol. 2011, 21, 339-442). Beside these fast cellular events, $GABA_B$ receptors also regulate cytoplasmic kinases including mitogen-activated protein kinase and thereby influence synaptic plasticity on the longer-term.

In order to better understand the physiological significance of $GABA_B$ receptors at the behavioral level, knockout mice have been generated with mutations selectively in the B1, B1a, B1b and the B2 subunits. Mice without B1 subunits displayed increased anxiety in explorative-like situations (light-dark box, staircase assays), increased panic, spontaneous seizures, hyperalgesia, hyperlocomotion, and memory impairment (Schuler et al, Neuron 2001, 31, 47-58). Mice that do not express $GABA_{B2}$ subunits behave similarly to B1 subunit knockouts; these animals are overanxious, show spontaneous seizure activity, hyperalgesia, hyperlocomotion, and memory impairment (Mombereau et al, Eur. J. Pharmacol. 2004, 497, 119-120; Mombereau et al, Neuroreport 2005, 16, 307-310; Gassmann et al, J. Neurosci. 2004, 24, 6086-6097). Based on the above, the $GABA_B$ receptor system seems to play a general role in the regulation of neuronal excitability with consequences on various aspects of overt behavior.

The only approved and commercialized selective $GABA_B$ receptor ligand is the orthosteric agonist racemic baclofen. Baclofen was approved as a centrally acting muscle relaxant used to reduce spasticity associated with cerebral palsy, multiple sclerosis, and spinal cord injuries. Beside these applications, baclofen may have potential therapeutic benefits in treating conditions including asthma, pain, obesity, binge eating, drug and alcohol abuse, anxiety, posttraumatic stress disorder, cough, inflammation, gastroeasophageal reflux and urinary incontinence (e.g., Breslow et al, Am. J. Psychiatry 1989, 146, 353-356; Drake et al, Ann. Pharmacother. 2003, 37, 1177-1181; Leggio et al, CNS Neurol. Disord. Drug Targets 2010, 9, 33-44). Although baclofen has beneficial potential in a number of therapeutic indications, unfortunately it also has a range of unwanted properties including poor blood-brain-barrier penetration, narrow therapeutic window, receptor desensitization, development of tolerance against the main effects, and withdrawal upon termination of use (Vacher and Bettler, Curr. Drug Targets CNS Neurol. Disord. 2003, 2, 248-259; Ross et al, Neurocrit. Care 2011, 14, 103-108; Keegan et al, Neuropharmacology 2015, 95, 492-502).

Allosteric modulation is an alternative way to selectively stimulate GPCRs without the unwanted properties of orthosteric ligands (Conn et al, Nat Rev 2009, 8, 41-54; Wang et al, J. Pharmacol. Exp. Ther. 2009, 331, 340-348). Allosteric modulators bind to the receptors at sites that are different from the binding site of the endogenous (orthosteric) ligands and are effective predominantly if an agonist is also bound to the receptor. This has consequences on the temporal and spacial pattern of efficacy which in turn affects the behavioral and adaptive responses the organism gives to allosteric stimulation. In contrast to orthosteric agonism, allosteric modulation of targets is expected to show less side effects, desensitization and development of tolerance. Indeed, it has been shown for the $GABA_B$ receptor positive allosteric modulator GS39783 in preclinical models, that this compound can have a favourable side effect profile (Cryan et al, *J. Pharmacol. Exp. Ther.* 2004, 310, 952-963), desensitization of the receptor can be prevented (Gjoni and Urwyler, *Neuropharmacology* 2008, 55:1293-1299) and tolerance may not develop upon chronic administration (Mombereau et al, *Neuropsychopharmacology* 2004, 29, 1050-1062). These results suggest that positive allosteric modulators of the $GABA_B$ receptor may be useful novel chemical entities without the unwanted properties of the orthosteric ligands such as baclofen.

Several patents and patent applications describe positive allosteric $GABA_B$ modulators which have different chemical structures. Pyrimidine derivatives as positive allosteric modulators of the $GABA_B$ receptor have been disclosed in WO 2005/094828 and WO 2006/136442. Thieno[3,2-b]pyrimidine and [1,3]thiazolo[5,4-d]pyrimidine derivatives as positive allosteric modulators of the $GABA_B$ receptor have been disclosed in WO 2015/056771 (US 2015/0111876).

A recent patent application by Faghih et al. (US 2016/0304527 A1) describes pyrazolo-pyrimidines with in vitro positive allosteric activity at the $GABA_B$ receptors measured by $[^{35}S]GTP\gamma S$ binding.

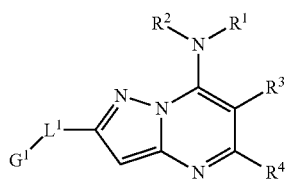

In Faghih et al. only one alicyclic-substituted compound with high micromolar binding potency has been demonstrated (Example 7-1), other exemplified compounds are aryl-substituted and show only micro or submicromolar binding potency. Unexpectedly, we found in the present invention that compounds with cyclohexyl moieties show nano or subnanomolar potency measured in a similar assay paradigm.

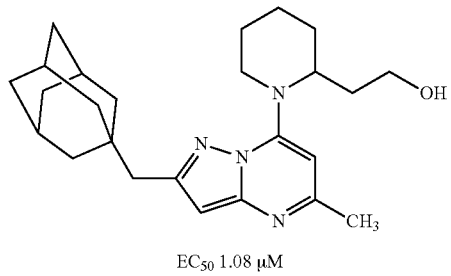

Example 7-1

$EC_{50}$ 1.08 µM

The invention of Faghih et al. describes that the incorporation of linkers comprising three or four carbon atoms (L1) increases in vitro potency. Most of the exemplified aryl-substituted compounds with linkers comprising one or two carbon atoms show only micro or submicromolar binding potency (Example 1-1). However, only the exemplified compounds which contain a linker comprising three or four carbon atoms (Example 3-1; Example 5-1) reach nanomolar potency. Unexpectedly, we found in the present invention that compounds without any linker show nano or subnanomolar potency.

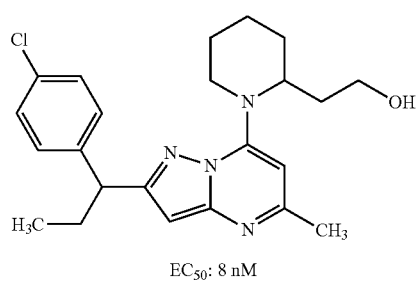

Example 3-1

$EC_{50}$: 8 nM

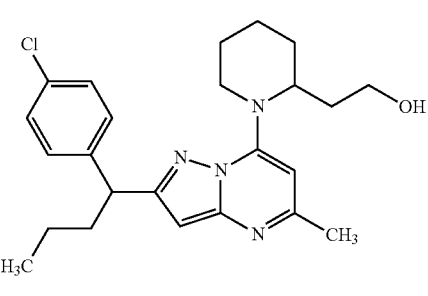

Example 5-1

$EC_{50}$: 3 nM

Examplified compounds containing azetidine carboxylic acid (Example 8-10) or nipecotic acid amide (Example 1-19) moieties in Faghih et al. show only high micromolar potency. Unexpectedly, we found in the present invention that compounds bearing simple nipecotic acid moiety show nano or subnanomolar potency. These compounds despite of possessing acidic nipecotic acid moiety are metabolically stable and unexpectedly penetrate into the brain (principles of brain penetration of drug molecules are summarized in: Kerns et al. Drug-like Properties: Concepts, Structure Design and Methods Chapter: Blood-Brain Barrier pages 122-136 "Figure 10.12: Acids poorly penetrate the BBB (Blood Brain Barrier) (CNS-)").

The above described in vitro advantages are further strengthened by the unexpected finding that selected compounds of the invention were of great behavioral benefit in the prenatal valproate disease model that recapitulates the core symptoms of autism spectrum disorder. The inventors therefore showed that this compound has therapeutic potential for the treatment of core symptoms of autism spectrum disorder in humans.

SUMMARY OF THE INVENTION

Our invention discloses nipecotic acid derivatives with a cyclohexyl-pyrazolo-pyrimidine scaffold. We found that these compounds show mostly nanomolar potency, in certain cases reaching even the subnanomolar potency range. These compounds despite of possessing acidic nipecotic acid moiety are metabolically stable and unexpectedly penetrate into the brain (principles of brain penetration of drug molecules are summarized in: Kerns et al. Drug-like Properties: Concepts, Structure Design and Methods Chapter: Blood-Brain Barrier pages 122-136). These compounds without having a carbon linker between the pyrazolo-pyrimidine core and the appended cyclohexyl ring show nanomolar potency. It was identified unexpectedly that an alkyl substituent at position 6 of the pyrazolo-pyrimydine scaffold (R3 in US20160304527) increased in vitro potency at least two order of magnitude. Our compounds show large effect sizes (reaching 80-100%) at low oral dosing (1 mg/kg) in an in vivo assay.

We have identified a class of pyrazolo[1,5-a]pyrimidine derivatives which have high affinity for $GABA_B$ receptors providing unique role in the treatment of psychiatric, neurodevelopmental, neurological and other central nervous system disorders as well as peripheral conditions where stimulation of the $GABA_B$ receptor may offer therapeutic benefit.

We identified new compounds that are brain penetrant. The present invention relates to compounds being $GABA_B$ receptor positive allosteric modulators and the synthesis thereof. Compounds of the present invention are useful for the treatment of psychiatric, neurodevelopmental, neurological and other central nervous system disorders as well as peripheral conditions where stimulation of the $GABA_B$ receptor may offer therapeutic benefit.

The present invention relates to the pyrazolo[1,5-a]pyrimidine derivatives of formula (I)

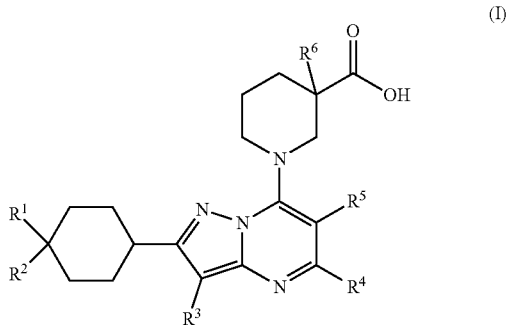

$R^1$ and $R^2$ are independently selected from hydrogen, halogen atom, $C_{1-6}$alkyl, halo$C_{1-6}$alkyl;
$R^3$ is hydrogen, halogen atom, $C_{1-6}$alkyl, cyano group;
$R^4$ is $C_{1-6}$alkyl;
$R^5$ is $C_{1-6}$alkyl optionally substituted by a halogen atom or halogen atoms, $C_{3-5}$ cycloalkyl;
$C_{3-5}$ cycloalkyl$C_{1-6}$alkyl, dialkylamino, $C_{1-6}$alkoxy, $C_{1-6}$alkoxy$C_{1-6}$alkyl, $C_{1-6}$alkylthio group, tetrahydrofuranyl, tetrahydrofuranyl$C_{1-6}$alkyl, tetrahydropyranyl, tetrahydropyranyl$C_{1-6}$alkyl; or $R_4$ and $R_5$ together form an unsubstituted or substituted by one or more $C_{1-3}$alkyl, $C_{1-3}$alkoxy, halo$C_{1-3}$alkyl, $C_{1-3}$alkylcarbonyl 3 to 7-membered saturated ring, wherein the members of the ring are selected from the group consisting of carbon, nitrogen, oxygen, and sulphur;
$R^6$ is hydrogen, halogen atom or $C_{1-6}$alkyl, hydroxyl, $C_{1-6}$alkoxy, $C_{1-6}$alkoxy$C_{1-6}$alkyl, halo$C_{1-6}$alkyl or amino group; or pharmaceutically acceptable salts, biologically active metabolites, pro-drugs, racemates, enantiomers, diastereomers, solvates and hydrates thereof.

The invention also relates to the pharmaceutical compositions containing the compounds of formula (I) or pharmaceutically acceptable salts, biologically active metabolites, pro-drugs, racemates, enantiomers, diastereomers, solvates and hydrates thereof.

Furthermore, the present invention relates to the synthesis of the compounds of formula (I) and optical antipodes or racemates and/or salts thereof, the pharmaceutical compositions comprising thereof and the chemical and pharmaceutical manufacture of medicaments containing these compounds, as well as the methods of treatment with these compounds, which means administering to a mammal to be treated—including human—suffering from psychiatric, neurodevelopmental, neurological and other central nervous system disorders as well as peripheral conditions where stimulation of the $GABA_B$ receptor may offer therapeutic benefit, effective amount of compounds of formula (I) and optical antipodes or racemates and/or salts thereof of the present invention as such or as medicament.

DETAILED DESCRIPTION OF THE INVENTION

The present invention relates to the pyrazolo[1,5-a]pyrimidine derivatives of formula (I)

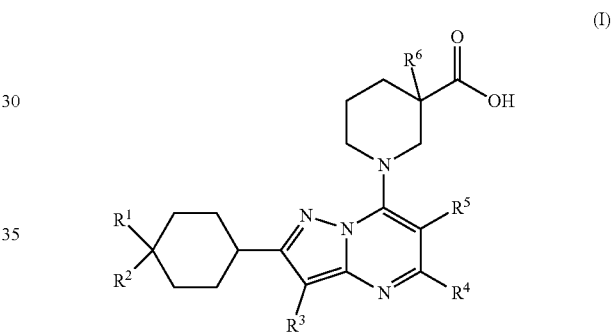

$R^1$ and $R^2$ are independently selected from hydrogen, halogen atom, $C_{1-6}$alkyl, halo$C_{1-6}$alkyl;
$R^3$ is hydrogen, halogen atom, $C_{1-6}$alkyl, cyano group;
$R^4$ is $C_{1-6}$alkyl;
$R^5$ is $C_{1-6}$alkyl optionally substituted by a halogen atom or halogen atoms, $C_{3-5}$ cycloalkyl;
$C_{3-5}$ cycloalkyl$C_{1-6}$alkyl, dialkylamino, $C_{1-6}$alkoxy, $C_{1-6}$alkoxy$C_{1-6}$alkyl, $C_{1-6}$alkylthio group, tetrahydrofuranyl, tetrahydrofuranyl$C_{1-6}$alkyl, tetrahydropyranyl, tetrahydropyranyl$C_{1-6}$alkyl; or $R_4$ and $R_5$ together form an unsubstituted or substituted by one or more $C_{1-3}$alkyl, $C_{1-3}$alkoxy, halo$C_{1-3}$alkyl, $C_{1-3}$alkylcarbonyl 3 to 7-membered saturated ring, wherein the members of the ring are selected from the group consisting of carbon, nitrogen, oxygen, and sulphur;
$R^6$ is hydrogen, halogen atom or $C_{1-6}$alkyl, hydroxyl, $C_{1-6}$alkoxy, $C_{1-6}$alkoxy$C_{1-6}$alkyl, halo$C_{1-6}$alkyl, amino group;
or pharmaceutically acceptable salts, biologically active metabolites, pro-drugs, racemates, enantiomers, diastereomers, solvates and hydrates thereof. The term "halogen" or "halo" as used herein alone or as a part of another group refers to chlorine, bromine, fluorine and iodine.

The term "$C_1$-$C_6$ alkyl" as used herein refers to branched or straight chain alkyl groups comprising one to six carbon atoms, including but not limited to methyl, ethyl, propyl, normal- and isopropyl and different butyl groups.

The term "$C_3$-$C_5$ cycloalkyl" as used herein refers to carbocyclic groups of 3 to 5 carbons, respectively; for example, cyclopropyl, cyclobutyl, and cyclopentyl.

The term "$C_1$-$C_6$ alkoxy" as used herein refers to branched or straight chain alkyl groups comprising one to four carbon atoms bonded through an oxygen atom, including but not limited to, methoxy, ethoxy, n-propoxy, i-propoxy, and t-butoxy.

The term "$C_{1-6}$alkylthio" as used herein refers to branched or straight chain alkyl groups comprising one to six carbon atoms bonded through a sulphur atom, including but not limited to, methylthio, ethylthio, n-propylthio, i-propylthio, and t-butylthio.

The term "mammal" as used herein refers to any members of the class "Mammalia" including, but not limited to human.

The term "salt" means nontoxic base addition salts of the compounds of the invention which are generally prepared by reacting the acid with a suitable organic or inorganic base.

Included within the scope of the present invention are all stereoisomers, geometric isomers and tautomeric forms of the compounds of formula (I), including compounds exhibiting more than one type of isomerism and mixtures of one or more thereof.

Conventional techniques for the preparation/isolation of individual enantiomers include chiral synthesis from the suitable optically pure precursor or resolution of the racemate (or racemate of a salt or derivative) using, for example chiral high pressure liquid chromatography (HPLC).

The term "pharmaceutically acceptable" describes an ingredient that is useful in preparing a pharmaceutical composition and is generally safe, non-toxic and neither biologically nor otherwise undesirable, and includes those acceptable for veterinary use as well as human pharmaceutical use.

The term "pharmaceutical composition" refers to a mixture of a compound of the invention with other chemical components, such as pharmaceutically acceptable auxiliary materials, e.g. diluents or carriers. The pharmaceutical composition facilitates administration of the compound to the subject.

The term "excipient" defines a chemical compound that facilitates the incorporation of a compound into cells or tissues.

As used herein, the term "treatment" means using an effective therapy to reduce, alleviate or eliminate the symptoms associated with diseases and conditions mediated and modulated by the $GABA_B$ receptor positive allosteric mechanism.

As a further aspect of the present invention there is provided the synthesis of compounds of formula (I).

Compounds according to the present invention were synthesized in line with the synthetic routes and schemes described below.

Accordingly, the compounds of formula (I) of the invention can be synthesized by one of the following routes:

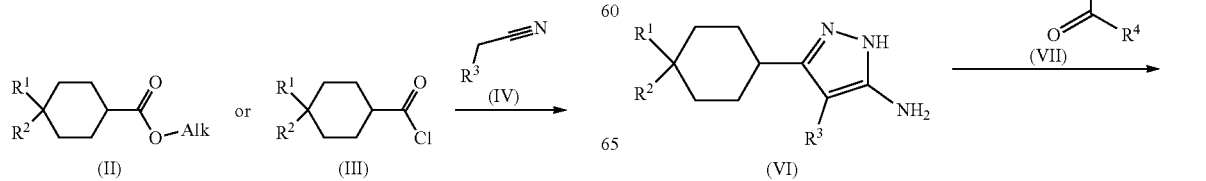

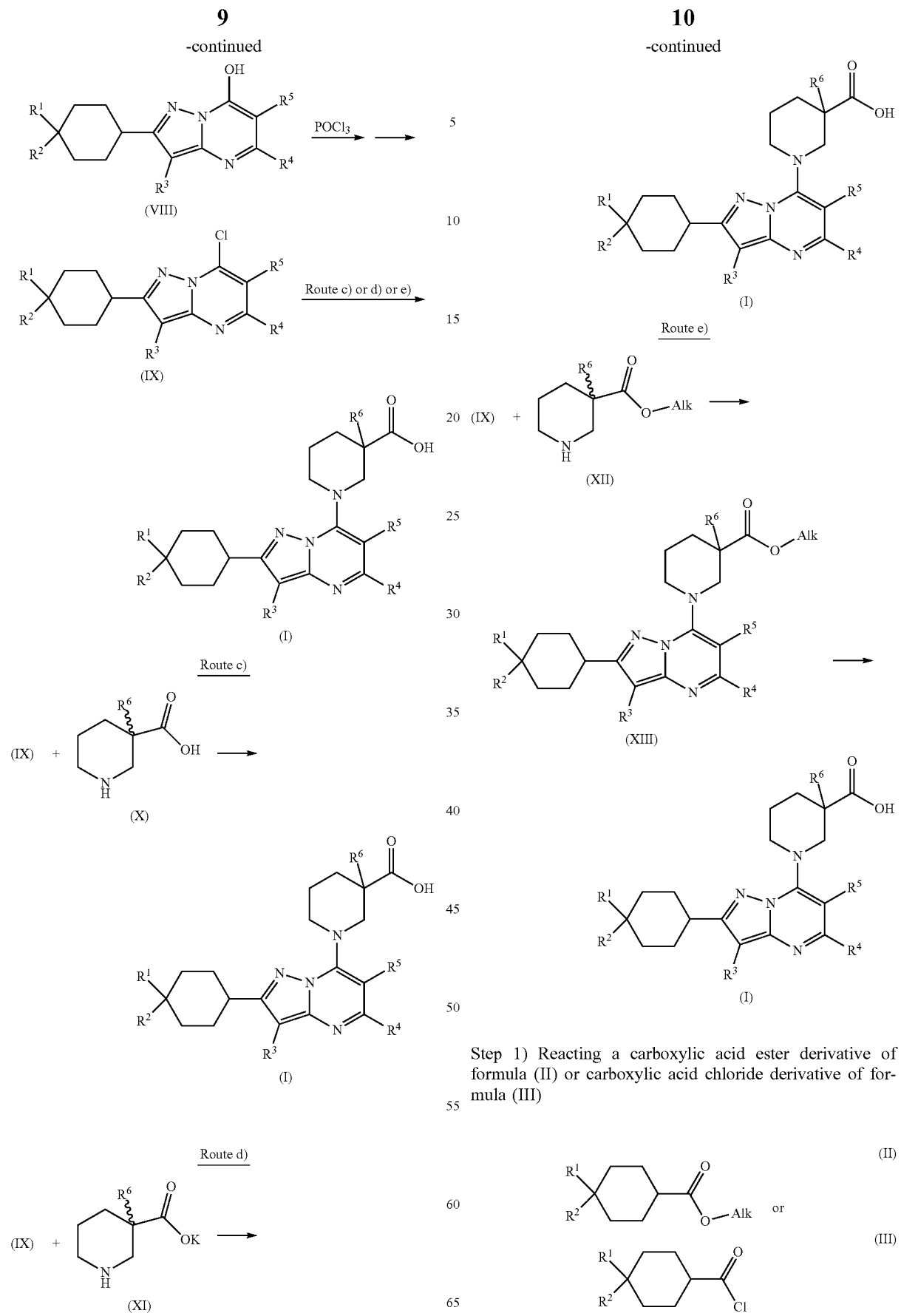

wherein the meaning of $R^1$ and $R^2$ is described above for compound of formula (I)—with an acetonitrile derivative of formula (IV)

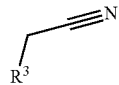
(IV)

wherein the meaning of $R^3$ is described above for compound of formula (I), then step 2) the so obtained acylacetonitrile derivative of formula (V) is reacted with

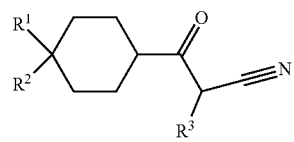
(V)

2a) hydrazine hydrate to provide a compound of formula (VI)

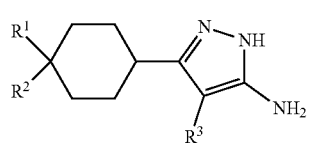
(VI)

wherein the meaning of $R^1$, $R^2$ is as described above and $R^3$ is hydrogen, halogen atom, $C_{1-6}$alkyl group or 2b) trimethyl orthoformate to provide the malononitrile derivative of formula (XIV)

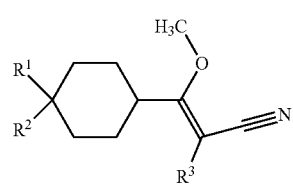
(XIV)

wherein the meaning of $R^1$, $R^2$ is as described above and $R^3$ is cyano group which is reacted with hydrazine hydrate to provide a compound of formula (VI) then

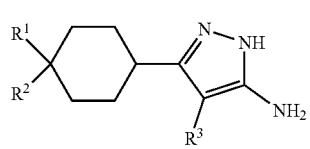
(VI)

step 3) the compound of formula (VI) wherein the meaning of $R^1$, $R^2$, $R^3$ is as described above for the formula (I)— obtained according to the steps described in 2a) or 2b) is reacted with acylacetic ester derivative of formula (VII)

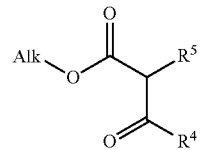
(VII)

wherein the meaning of $R^4$ and $R^5$ is as described above for the formula (I), then step 4) the so obtained compound of formula (VIII)

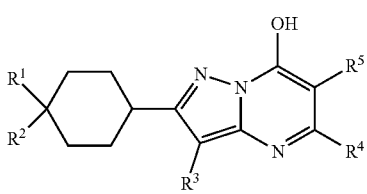
(VIII)

wherein the meaning of $R^1$, $R^2$, $R^3$, $R^4$, and $R^5$ is as described above for the formula (I)—is chlorinated to furnish a chloro derivative of formula (IX)

(IX)

wherein the meaning of $R^1$, $R^2$, $R^3$, $R^4$, and $R^5$ is as described above for the formula (I)—and step 5) the latter is reacted with either 5c) a nipecotic acid derivative of formula (X)

(X)

wherein the meaning of $R^6$ is as described above for the formula (I)—and the obtained derivative of formula (I) and optical antipodes or racemates and/or salts thereof in given case can be transformed into an other compound of formula (I) and optical antipodes or racemates and/or salts thereof by introducing new substituents and/or modifying or removing the existing ones, or 5d) its alkali salt of formula (XI)

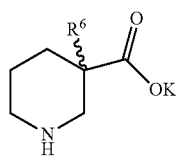
(XI)

wherein the meaning of $R^6$ is as described above for the formula (I)—and the obtained compound of formula (I) and optical antipodes or racemates and/or salts thereof in given case can be transformed into an other compound of formula (I) and optical antipodes or racemates and/or salts thereof by introducing new substituents and/or modifying or removing the existing ones, or 5e) a nipecotic acid ester derivative of formula (XII)

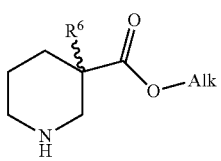
(XII)

wherein the meaning of $R^6$ is as described above for the formula (I)—to provide the ester derivative of formula (XIII)

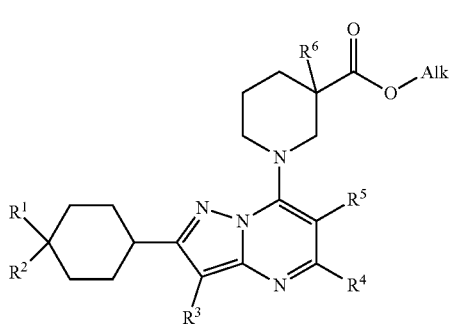
(XIII)

wherein the meaning of $R^1$, $R^2$, $R^3$, $R^4$, $R^1$ and $R^6$ is as described above for the formula (I) finally the latter is saponified with a strong base or acid—and the obtained derivative of formula (I) and optical antipodes or racemates and/or salts thereof optionally can be transformed into an other compound of formula (I) and optical antipodes or racemates and/or salts thereof by introducing new substituents and/or modifying or removing the existing ones.

The synthesis of acylacetonitrile derivative (V) can be carried out by different routes:

Route a):

a) The reaction of a carboxylic acid ester derivative of formula (II) with an acetonitrile derivative of formula (IV) is preferably carried out in a proper solvent, e.g. tetrahydrofuran, preferably in the presence of a strong base e.g. n-butyllithium, lithium bis(trimethylsilyl)amide. The reaction carried out at a temperature in the range of −78° C. to room temperature. The necessary reaction time is 1-16 h. The reactions are followed by thin layer chromatography. The reaction is quenched by addition of water and hydrochloric acid (~pH 2-3) or saturated ammonium chloride solution. The product (V) is isolated by extraction with a proper organic solvent or by filtration, after removing the organic solvent.

b) The reaction of an carboxylic acid chloride derivative of formula (III) with an acetonitrile derivative of formula (IV) is preferably carried out in a proper solvent, e.g. tetrahydrofuran, preferably in the presence of a strong base e.g. n-butyllithium, lithium bis(trimethylsilyl)amide. The reaction carried out at a temperature in the range of −78° C. to room temperature. The necessary reaction time is 1-16 h. The reactions are followed by thin layer chromatography. The reaction is quenched by addition of water and hydrochloric acid (~pH 2-3) or saturated ammonium chloride solution. The product (V) is isolated by extraction with a suitable organic solvent or by filtration, after removing the organic solvent.

The cyclocondensation reaction of the acyl nitrile derivatives of formula (V) with hydrazine hydrate to pyrazole derivatives of formula (VI) is preferably carried out in a suitable solvent, e.g. ethanol. The reaction is preferably carried out at boiling point of the solvent. The necessary reaction time is 1-6 h. The reactions are followed by thin layer chromatography. The work-up of the reaction mixture can be carried out by the following routes:

a) The reaction mixture is diluted with water and the product is isolated by filtration or extraction with a suitable organic solvent and in given case purified by crystallization or column chromatography.

b) The reaction mixture is evaporated in vacuo and the crude product is used in the next step without further purification.

Route b):

The reaction of a carboxylic acid chloride derivative of formula (III) with malononitrile is preferably carried out in a suitable solvent, e.g. tetrahydrofuran, preferably in the presence of a base e.g. triethylamine. The reaction carried out at a temperature in the range of 0° C. to room temperature. The necessary reaction time is 1-16 h. The reactions are followed by thin layer chromatography. The reaction is quenched by addition of water. The product (V) is isolated by extraction with a suitable organic solvent.

The O-methylation of the acyl malononitrile derivative of formula (V) with trimethyl orthoformate is preferably carried out at boiling point. The necessary reaction time is 1-16 h. The reactions are followed by thin layer chromatography. The product (XIV) is purified by column chromatography.

The cyclocondensation reaction of the O-methylated acyl nitrile derivatives of formula (XIV) with hydrazine hydrate to pyrazole derivatives of formula (VI) is preferably carried out in a suitable solvent, e.g. ethanol. The reaction is preferably carried out at room temperature. The necessary reaction time is 1-6 h. The reactions are followed by thin layer chromatography. The reaction mixture is diluted with water and the product is isolated by extraction with a suitable organic solvent.

The cyclocondensation reaction of the 1H-pyrazol-5-amine derivative of formula (VI) with an acylacetic ester derivative of formula (VII) is preferably carried out in a suitable solvent, e.g. toluene, by the addition of catalytic amount of p-toluenesulfonic acid, using a Dean-Stark water separator. The reaction is preferably carried out at boiling point of the solvent. The necessary reaction time is 1-16 h. The reactions are followed by thin layer chromatography. The product (VIII) is isolated by filtration.

Chlorination of the pyrazolo[1,5-a]pyrimidine derivative of formula (VIII) can be carried out in a suitable solvent, e.g. toluene using a suitable chlorinating agent, e.g. phosphorus oxychloride by the addition of triethylamine or N,N-diisopropylethylamine. The reaction is preferably carried out at boiling point of the solvent. The necessary reaction time is 24-48 h. The reactions are followed by thin layer chromatography. The reaction mixture is poured into sodium hydrogen carbonate solution and crushed ice. The decomposed reaction mixture is filtered and the product is isolated from the filtrate by extraction with a suitable organic solvent and in given case purified by crystallization or column chromatography. The column chromatography is carried out on normal phase using Kieselgel 60 as adsorbent and different solvent systems, e.g. n-hexane/ethyl acetate, toluene/methanol, chloroform/methanol or toluene/acetone, as eluents.

N-arylation reaction of the nipecotic acid derivative of formula (X) or (XII) with the chloro derivative of formula (IX) carried out in a suitable solvent, e.g. dimethylformamide, dimethylsulfoxide, N-methyl-pyrrolidone. The reaction is preferably carried out between 80° C. and 140° C. A suitable amine of formula (X) or (XII) is added as base or as a salt formed with inorganic acid to the so obtained solution in the presence of a base, for example cesium carbonate or N,N-diisopropylethylamine, needed for the liberation of the amine or formed with inorganic base for example potassium salt of formula (XI). The reactions are followed by thin layer chromatography. The necessary reaction time is 3-20 h. The work-up of the reaction mixture can be carried out by different methods.

When the N-arylated product is an acid derivative of formula (I) and the reaction mixture is a suspension, the inorganic salt is filtered off, the filtrate is diluted with water and acidified with acetic acid. The product is isolated by filtration or extraction with a suitable organic solvent and in given case purified by crystallization or column chromatography. If the reaction mixture is a solution, it is diluted with water and acidified with acetic acid. The product is isolated by filtration or extraction with a suitable organic solvent and in given case purified by crystallization or column chromatography.

When the N-arylated product is an ester derivative of formula (XIII), the reaction mixture is evaporated in vacuo. The product is isolated by crystallization or extraction with a suitable organic solvent and in given case purified by recrystallization or column chromatography.

The hydrolysis of the carboxylic acid ester derivative of formula (XIII) into the carboxylic acid derivative of formula (I) can be carried out with an appropriate strong inorganic base, e.g. lithium hydroxide, sodium hydroxide or with an appropriate strong inorganic acid, e.g. hydrochloric acid. The reaction is preferably carried out between room temperature and 100° C. The reactions are followed by thin layer chromatography. The necessary reaction time is 1-20 h. The reaction mixture is diluted with water and acidified with acetic acid. The product is isolated by filtration or extraction with a suitable organic solvent and in given case purified by crystallization or column chromatography. The structures of the products are determined by NMR and mass spectrometry.

Most of the nipecotic acid derivatives of formula (X) and (XII) are either commercially available or can be synthesized by different known methods. The syntheses of some new nipecotic acid derivatives of formula (XII) are described in the Intermediates section.

The compounds of the present invention and optical antipodes or racemates and/or salts thereof can be used as such or suitably in the form of pharmaceutical compositions.

The invention also relates to the pharmaceutical compositions containing the compounds of formula (I) or optical antipodes or racemates and/or salts thereof as active ingredient for the treatment of certain disorders associated with $GABA_B$ receptor positive allosteric modulator activity.

The present compounds may be coadministered to a subject in combination with two or more different therapeutic agents (e.g. most preferably antipsychotics and psychostimulants; and preferably antidepressants, anxiolytics, antihypertensives, anticonvulsants, sedatives, and narcotics).

Suitable routes of administration may, for example, include oral, rectal, transmucosal, transdermal or intestinal administration; parenteral delivery, including intramuscular, subcutaneous, intravenous, intramedullary injections, as well as intraarticular, intrathecal, direct intraventricular, intraperitoneal, intranasal, or intraocular injections and eye drops.

Alternatively, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions can be administered through via a variety of routes and dosages forms. The compound of the invention may be administered either alone or in combination with pharmaceutically acceptable carriers, in either single or multiple doses. The dosage required to exert the therapeutic effect can vary within wide limits and will be fitted to the individual requirements in each of the particular case, depending on the stage of the disease, the condition and the bodyweight of the patient to be treated, as well as the sensitivity of the patient against the active ingredient, route of administration and number of daily treatments.

For the sake of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

The pharmaceutical compositions containing the active ingredient according to the present invention usually contain 0.01 to 500 mg of active ingredient in a single dosage unit. It is, of course possible that the amount of the active ingredient in some compositions exceeds the upper or lower limits defined above.

As a further aspect of the invention there is provided the pharmaceutical manufacture of medicaments containing the compounds of formula (I) or optical antipodes or racemates and/or salts thereof.

The pharmaceutical compositions of the present invention may be formulated as different pharmaceutical dosage forms, such as but not limited to, solid oral dosage forms like tablets (e.g. buccal, sublingual, effervescents, chewable, orodispersible, freeze dried), capsules, lozenges, pastilles, pills, orodispersible films, granules, powders; liquid oral dosage forms like solutions, emulsions, suspensions, syrups, elixires, oral drops; parenteral dosage forms like intravenous injections, intramuscular injections, subcutaneous injections; other dosage forms like eye drops, semi-solid eye preparations, transdermal dosage forms, suppositories, rectal capsules, rectal solutions, emulsions and suspensions, etc.

In one embodiment the invention relates to pharmaceutical dosage forms specifically intended for pediatric use, such as but not limited to, solutions, syrups, elixirs, suspensions, powders for reconstitution as suspension, dispersible or effervescent tablets, chewable tablets, orally disintegrating tablets, tablets or coated tablets, sprinkle oral powder or granules, capsules.

The pharmaceutical compositions of the present invention may be manufactured in a manner that is itself known, e.g., by means of conventional mixing, dissolving, emulsifying, suspending, entrapping, freeze-drying, extrusion, laminating, film-casting, granulating, grinding, encapsulating, dragee-making or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art.

Suitable excipients for the preparation of the dosage forms may be selected from the following categories, such as but not limited to, tablet and capsule fillers, tablet and capsule binders, modified-release agents, disintegrants, glidants, lubricants, sweetening agents, taste-masking agents, flavoring agents, coating agents, surfactants, antioxidants, buffering agents, complexing agents, emulsifying agents, lyophilization aids, microencapsulating agents, ointment bases, penetration enhancers, solubilizing agents, solvents, suppository bases, suspending agents.

In one embodiment the invention relates to the using of specific excipients which are able to improve the solubility, dissolution, penetration, adsorption or bioavailability of the active ingredient(s), such as but not limited to, hydrophilic polymers, hot melt extrusion excipients, surfactants, buffering agents, complexing agents, emulsifying agents, lyophilization aids, superdisintegrants, microencapsulating agents, penetration enhancers, solubilizing agents, co-solvents, suspending agents.

The above described ingredients and different routes of manufacture are merely representative. Other materials as well as processing techniques and the like well known in the art can also be used.

The compounds are effective in the treatment of psychiatric, neurodevelopmental, neurological and other central nervous system disorders as well as peripheral conditions where stimulation of the $GABA_B$ receptor may offer therapeutic benefit Biological Activity In Vitro [$^{35}$S]GTPγS Binding Assay in Rat Cortical Membranes Cortices of freshly harvested rat brains were dissected on an ice-cold surface and homogenized by a glass Dounce homogeniser immediately in ice-cold buffer containing 50 mM Tris, 5 mM $MgCl_2$ and 1 mM EDTA (pH=7.6). Tissue homogenates were centrifuged at 40000 g for 15 min at 4° C. Membrane pellets were resuspended in the same buffer and membranes were incubated for 10 min at 30° C. in a shaking water bath to eliminate endogenous GABA. Homogenates were centrifuged again under the same conditions. The final pellets were resuspended in ice-cold buffer (pH=7.6) containing 50 mM Tris, 100 mM NaCl, 7 mM $MgCl_2$, 1 mM EDTA and 1 mM dithiotreithol (DTT) to yield a concentration of 20 mg tissue weight/ml and frozen at −70° C. until use. The assay was done in a buffer containing 50 mM Tris (pH=7.4), 100 mM NaCl, 7 mM $MgCl_2$, 1 mM EDTA and 1 mM DTT. Each assay tube contained 150 μL GDP (in a final concentration of 50 μM), 100 μL ligand and 125 μL of the membrane suspension (250 μg tissue/tube). The assay tubes were preincubated for 10 min at 30° C. to assure equilibrium. Nonspecific binding was determined in the presence of 10 μM GTPγS: basal binding was determined in the presence of buffer only. After addition of 50 pM [$^{35}$S]GTPγS in a volume of 25 μL to the tubes, membranes were incubated for an additional 60 min at 30° C. The assay was terminated by rapid filtration through Packard UniFilter GF/B using a Packard harvester and washed four times with 1 ml ice-cold buffer. After drying the filters at 40° C. for 1 h, 40 μL Microscint (Packard) was added to the filters and radioactivity of the filters was determined by a TopCount NXT (PerkinElmer, Waltham, Mass.: Alper and Nelson, *Eur. J. Pharmacol.* 1998, 343, 303-312; Rinken et al, *Biochem. Pharmacol.* 1999, 57, 155-162). Data thus gathered were used to determine PAM $EC_{50}$ values for each compound as primary in vitro activity end point.

In Table 1 compounds of this invention measured in the [$^{35}$S]GTPγS binding assay are listed.

TABLE 1

| Number of example | In vitro PAM potency |
|---|---|
| 1 | ++ |
| 2 | ++ |
| 3 | + |
| 4 | ++ |
| 5 | ++ |
| 6 | ++ |
| 7 | + |
| 10 | ++ |
| 11 | ++ |
| 12 | ++ |
| 13 | + |
| 14 | ++ |
| 15 | ++ |
| 16 | + |
| 17 | ++ |
| 18 | + |
| 19 | +++ |
| 20 | ++++ |
| 21 | +++ |
| 22 | ++++ |
| 23 | ++ |
| 24 | +++ |
| 25 | +++ |
| 26 | +++ |
| 27 | ++ |
| 28 | +++ |
| 29 | +++ |
| 30 | ++ |
| 31 | +++ |
| 32 | +++ |
| 34 | ++ |
| 35 | ++ |
| 36 | ++++ |
| 37 | ++++ |
| 40 | ++ |
| 42 | ++++ |

+ PAM $EC_{50}$ < 1 nM
++ 1 nM ≤ PAM $EC_{50}$ < 10 nM
+++ 10 ≤ PAM $EC_{50}$ < 100 nM
++++ 100 ≤ PAM $EC_{50}$ < 1000 nM

Foot Shock-Induced Ultrasonic Vocalization (USV) in Adult Rats

Under stressful conditions, adult rats emit 22 kHz ultrasounds that can be reduced by various pharmacological treatments (De Vry et al, Eur. J. Pharmacol. 1993, 249, 331-339; Sanchez, Eur. J. Pharmacol. 2003, 463, 133-143). Previous unpublished experiments indicated that $GABA_B$ receptor ligands can also inhibit vocalizatons that are induced by electric footshocks as stressor. Therefore, a foot shock-induced vocalization paradigm in adult rats was used to assess efficacy of centrally acting $GABA_B$ receptor ligands. Behavioral measurements were carried out on male Wistar rats (200-250 g, Toxicoop, Hungary). Rats were housed in groups of four in plastic cages with a wire grid top in a temperature and light-controlled laboratory animal care unit (22±2° C., 12-h light/dark cycle, lights on at 6:00 AM) with ad libitum access to commercial pellet rat food and tap water. Investigations were approved by the Local Ethical Committee of Gedeon Richter Plc. and were carried out in strict compliance with the European Directive 2010/63/EU regarding the care and use of laboratory animals for experimental procedures and all efforts were made to minimize the number of animals as well as their suffering. In order to evoke emission of ultrasounds, animals were footshocked after a habituation period of 30 s (6 shocks, 1 s, 0.8 mA each, inter-shock interval 10 s) in a sound attenuated shocking chamber (Experimetria, 40×40×80 cm). Investigational compounds were administered at the dose of 1 mg/kg in a solid dispersion formulation in distilled water 1 h before shocking per os. Vocalizations were measured right after the last footshock for 10 min with a Metris Sonotrack system and the total time of vocalizations was registered. Vocalization of parallel vehicle treated animals was considered as control value and inhibition percent was calculated for each compound. At approximately 75 min after treatment and behavioral measurements, blood and brain samples were harvested in order to determine exposures associated with in vivo activity.

In Table 2 compounds of this invention measured in the USV assay are listed. In Table 3 plasma and brain levels of compounds of this invention are listed.

TABLE 2

| Number of example | USV inhibition at 1 mg/kg (%) |
| --- | --- |
| 2 | 85 |
| 3 | 100 |
| 11 | 71 |
| 12 | 59 |
| 13 | 97 |
| 15 | 89 |
| 16 | 100 |
| 17 | 79 |
| 18 | 75 |
| 33 | 63 |
| 35 | 57 |

TABLE 3

| Number of example | plasma exposure at 1 mg/kg (ng/mL) | brain exposure at 1 mg/kg (ng/g) |
| --- | --- | --- |
| 2 | 188 | 74 |
| 3 | 58 | 18 |
| 11 | 146 | 68 |
| 12 | 121 | 62 |
| 13 | 124 | 31 |
| 15 | 170 | 53 |
| 16 | 131 | 36 |
| 17 | 135 | 74 |
| 18 | 175 | 30 |
| 33 | 172 | 34 |
| 35 | 207 | 35 |

Prenatal Valproate Model of Autism Spectrum Disorder (ASD)

The prenatal valproate model has excellent construct and face validity, therefore it is a widely accepted disease model of ASD (Christensen et al, *JAMA* 2013, 309, 1696-1703; Roullet et al, *Neurotox. Teratol.* 2013, 36, 45-56). In this method, time-mated female Wistar rats (Harlan UK) were administered a single dose of valproic acid (VPA, 600 mg/kg, i.p.) on gestational day 12.5. Male offspring were housed according to standard laboratory conditions until time of testing at postnatal day 59. Animals were housed in groups of 4 in conventional cages and maintained at 22-24° C. on a standard 12 hour light/dark cycle (07.30-19.30), with food and water available ad libitum. After investigational drug treatment, offspring were examined behaviorally in the social preference assay at postnatal day 59. The social preference test is a highly accepted assay to assess autistic behavior in rodents (Nadler et al, *Genes Brain Behav.* 2007, 3, 303-314; Bambini-Junior et al, *Brain Res.* 2011, 1408, 8-16). Briefly, in this assay a test animal is allowed to investigate a conspecific separated by a dividing perforated wall or a similar area however, without a target conspecific. An autistic animal (such as a prenatally valproate-exposed rat) spends little time with social investigation during a test session.

The inventors unexpectedly found that selected compounds of the invention in the oral dose range of 0.01-3 mg/kg were of great behavioral benefit in the present preclinical disease model that recapitulates the core symptoms of ASD. The inventors therefore showed that these compounds may be of therapeutic potential for the treatment of core symptoms of ASD in humans.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In general, the compounds of formula (I) can be prepared according to the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art.

Our patent application filed concurrently herewith titled "Process for the separation of optical isomers of racemic 3-alkylpiperidine-carboxylic acid ethyl esters" discloses the preparation of certain starting materials.

The present invention will be now illustrated by the following not limiting examples.

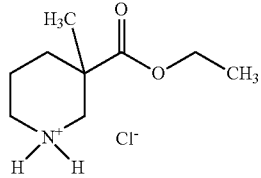

Intermediate 1

Ethyl 3-methylpiperidine-3-carboxylate a) 1-Tert-butyl 3-ethyl 3-methylpiperidine-1,3-dicarboxylate Under nitrogen to a solution of 22.96 g (89 mmol) of 1-tert-butyl 3-ethyl piperidine-1,3-dicarboxylate in 300 mL of dry tetrahydrofuran 100 mL of 1 M lithium bis(trimethylsilyl)amide in tetrahydrofuran solution (100 mmol) was added dropwise at (−78)° C.-(−65) ° C. After addition the mixture was stirred at −78° C. for 20 min, 6.6 mL (106 mmol) of iodomethane was added dropwise. The so obtained mixture was allowed to warm to room temperature and stirred at this temperature for 18 h. The reaction was quenched by addition of 200 mL of saturated ammonium chloride solution (pH ~8) and 300 mL of water. The reaction mixture was extracted with ethyl acetate, the combined organic layer was washed with water, dried over anhydrous sodium sulfate, filtered and concentrated in vacuo. The residue was chromatographed on silica gel eluting with ethylacetate and cyclohexane (1:4) to yield 24.2 g (95%) of the title compound as oil.

b) Ethyl 3-methylpiperidine-3-carboxylate

To a solution of 50 ml of 2.5 M hydrochloric acid in ethyl acetate 24.2 g (84.8 mmol) of 1-tert-butyl 3-ethyl 3-methylpiperidine-1,3-dicarboxylate was added. The reaction mixture was stirred for 3 h at 20° C., then 100 mL of diethyl ether was added. The precipitated crystals were filtered off, washed with diethyl ether to yield 16.28 g (97%) of the title compound.

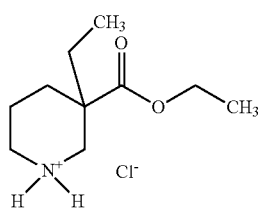

Intermediate 2

Ethyl 3-ethylpiperidine-3-carboxylate a) 1-tert-Butyl 3-ethyl 3-ethylpiperidine-1,3-dicarboxylate The title compound is prepared from 1-tert-butyl 3-ethyl piperidine-1,3-dicarboxylate and iodo ethane according to the method described in Intermediate 1a.

b) Ethyl 3-ethylpiperidine-3-carboxylate hydrochloride

The title compound is prepared from 1-tert-butyl 3-ethyl 3-ethylpiperidine-1,3-dicarboxylate according to the method described in Intermediate 1b.

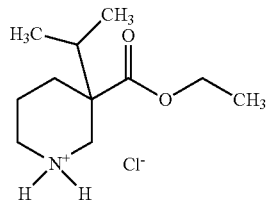

Intermediate 3

Ethyl 3-(propan-2-yl)piperidine-3-carboxylate Hydrochloride a) 1-tert-Butyl 3-ethyl 3-(propan-2-yl)piperidine-1,3-dicarboxylate The title compound is prepared from 1-tert-butyl 3-ethyl piperidine-1,3-dicarboxylate and 2-iodo propane according to the method described in Intermediate 1a.

b) Ethyl 3-(propan-2-yl)piperidine-3-carboxylate

The title compound is prepared from 1-tert-butyl 3-ethyl 3-(propan-2-yl)piperidine-1,3-dicarboxylate according to the method described in Intermediate 1b.

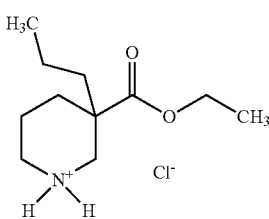

Intermediate 4

Ethyl 3-propylpiperidine-3-carboxylate Hydrochloride a) 1-Tert-butyl 3-ethyl 3-propylpiperidine-1,3-dicarboxylate Under nitrogen to a solution of 10 g (38.86 mmol) of 1-tert-butyl 3-ethyl piperidine-1,3-dicarboxylate in 120 mL of dry tetrahydrofuran 42 mL of 1 M lithium bis(trimethylsilyl)amide in tetrahydrofuran solution (42 mmol) was added dropwise at (−78)° C.-(−65)° C. After addition the mixture was stirred at −78° C. for 20 min, 3.9 mL (39.7 mmol) of 1-iodopropane was added dropwise. The so obtained mixture was allowed to warm to room temperature and stirred at this temperature for 18 h. The reaction was quenched by addition of 200 mL of saturated ammonium chloride solution (pH ~8) and 300 mL of water. The reaction mixture was extracted with ethyl acetate, the combined organic layer was washed with water, dried over anhydrous sodium sulfate, filtered and concentrated in vacuo. The residue was chromatographed on silica gel eluting with ethylacetate and cyclohexane (1:4) to obtain the title compound as oil. The crude product is used in the next step.

b) Ethyl 3-propylpiperidine-3-carboxylate Hydrochloride

To the above obtained 1-tert-butyl 3-ethyl 3-propylpiperidine-1,3-dicarboxylate 20 ml of 2.5 M hydrochloric acid in ethyl acetate was added. The reaction mixture was stirred for 3 h at 20° C., then concentrated in vacuo to yield 11.85 g of the title compound as oil.

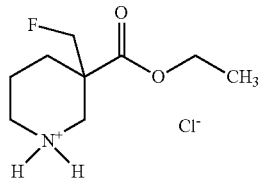

Intermediate 5

Ethyl 3-(fluoromethyl)piperidine-3-carboxylate Hydrochloride a) 1-tert-Butyl 3-ethyl 3-(hydroxymethyl)piperidine-1,3-dicarboxylate The title compound is prepared from 1-tert-butyl 3-ethyl piperidine-1,3-dicarboxylate and paraformaldehyde according to the method described in Intermediate 1a.

b) 1-tert-Butyl 3-ethyl 3-{[(1,1,2-trifluoroethanesulfonyl)oxy]methyl}piperidine-1,3-dicarboxylate Under nitrogen, to a stirred solution of 0.296 g (1.03 mmol) of ethyl 3-(hydroxymethyl) piperidine-3-carboxylate and 0.120 ml (1.48 mmol) of pyridine in 5 ml of dichloromethane 0.230 ml (1.48 mmol) of trifluoromethanesulfonic anhydride was added dropwise at (−78)° C.-(−65)° C. After addition the mixture was stirred at −78° C. for 5 min and allowed to warm to room temperature and stirred at this temperature for 18 h. The reaction was quenched by addition of 1M hydrochloric acid solution. The reaction mixture was extracted with dichloromethane, the combined organic layer was washed with water, dried over anhydrous sodium sulfate, filtered and concentrated in vacuo to obtain the title compound as oil. The crude product is used in the next step.

c) 1-tert-Butyl 3-ethyl 3-(fluoromethyl)piperidine-1,3-dicarboxylate

The above obtained 1-tert-butyl 3-ethyl 3-{([(1,1,2-trifluoroethanesulfonyl)oxy]methyl}piperidine-1,3-dicarboxylate was solved in 4 ml of tetrahydrofuran and 1.25 ml (1.25 mmol) of 1M tetrabutylammonium fluoride in tetrahydrofuran was added. The reaction mixture was stirred for 1 h at room temperature, diluted with water and extracted with ethylacetate. The combined organic layer was washed with water, dried over anhydrous sodium sulfate, filtered and concentrated in vacuo. The residue was chromatographed on silica gel eluting with ethylacetate and cyclohexane (1:2) to yield 0.121 g (40%) of the title compound.

d) Ethyl 3-(fluoromethyl)piperidine-3-carboxylate Hydrochloride

The title compound is prepared from 1-tert-Butyl 3-ethyl 3-(fluoromethyl)piperidine-1,3-dicarboxylate according to the method described in Intermediate 1b.

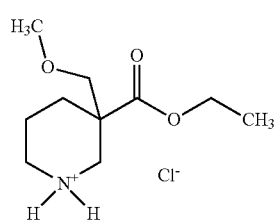

Intermediate 6

Ethyl 3-(methoxymethyl)piperidine-3-carboxylate Hydrochloride a) 1-tert-Butyl 3-ethyl 3-(methoxymethyl)piperidine-1,3-dicarboxylate The title compound is prepared from 1-tert-butyl 3-ethyl piperidine-1,3-dicarboxylate and chloromethyl methyl ether according to the method described in Intermediate 1a.

b) Ethyl 3-(methoxymethyl)piperidine-3-carboxylate hydrochloride

The title compound is prepared from 1-tert-butyl 3-ethyl 3-(methoxymethyl)piperidine-1,3-dicarboxylate according to the method described in Intermediate 1b.

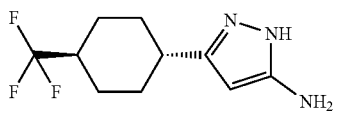

Intermediate 7

3-[trans-4-(Trifluoromethyl)cyclohexyl]-1H-pyrazol-5-amine a) Methyl trans-4-(trifluoromethyl)cyclohexane-1-carboxylate To a solution of 10 g (51 mmol) of trans 4-(trifluoromethyl)cyclohexane-1-carboxylic acid in 150 ml of methanol 10 ml (137 mmol) of thionyl chloride was added dropwise at −10° C. After addition the mixture was allowed to warm to room temperature and stirred at this temperature for 16 h, then concentrated in vacuo. The residue was partitioned between ethyl acetate and water. The combined organic layer was washed with sodium hydrogene carbonate solution and water, dried over anhydrous sodium sulfate, filtered and concentrated in vacuo. Dry cyclohexane was evaporated from the residue several times to yield 8.96 g of the title compound as colourless oil.

b) 3-Oxo-3-[trans-4-(trifluoromethyl)cyclohexyl]propanenitrile

Under nitrogen to a mixture of 9.1 ml (174 mmol) of acetonitrile in 260 ml of dry tetrahydrofuran 51 ml of 2.5 M n-butyllithium in n-hexane solution (127 mmol) was added dropwise at (−78)° C.-(−65)° C. After addition the mixture was stirred at −78° C. for 1 h, 8.96 g (42.6 mmol) of methyl trans-4-(trifluoromethyl)cyclohexane-1-carboxylate was added dropwise. The so obtained mixture was allowed to warm to room temperature and stirred at this temperature for 1 h. The reaction was quenched by addition of 150 mL of saturated ammonium chloride solution. The tetrahydrofuran was evaporated and the mixture was extracted with ethyl acetate. The combined organic layer was washed with water, dried over anhydrous sodium sulfate, filtered and concentrated in vacuo. The crude product is used in the next step.

c) 3-[trans-4-(Trifluoromethyl)cyclohexyl]-1H-pyrazol-5-amine

The above obtained 3-oxo-3-[trans-4-(trifluoromethyl)cyclohexyl]propanenitrile was solved in 187 ml of ethanol and 4.4 ml (167 mmol) of hydrazine monohydrate was added. Under inert gas atmosphere, the reaction mixture was refluxed for 16 h. The solvent was removed in vacuo and dry toluene was evaporated from the residue several times to yield 11.15 g of the title compound as yellow oil. LC-MS (ESI) m/z 234.2 [MH$^+$]

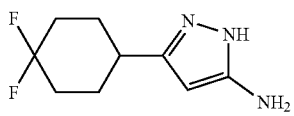

3-(4,4-Difluorocyclohexyl)-1H-pyrazol-5-amine a) 3-(4,4-Difluorocyclohexyl)-3-oxopropanenitrile Under nitrogen to a mixture of 5 mL (95.7 mmol) of acetonitrile in 150 ml of dry tetrahydrofuran 29 ml of 2.5 M n-butyllithium in n-hexane solution (72.5 mmol) was added dropwise at (−78)° C.-(−65)° C. After addition the mixture was stirred at −78° C. for 1 h, 4.2 ml (24 mmol) of ethyl 4,4-difluorocyclohexane-1-carboxylate was added dropwise. The so obtained mixture was allowed to warm to room temperature and stirred at this temperature for 2 h. The reaction was quenched by addition of 150 mL of saturated ammonium chloride solution and the mixture was extracted with ethyl acetate. The combined organic layer was washed with water, dried over anhydrous sodium sulfate, filtered and concentrated in vacuo. The crude product is used in the next step.

b) 3-(4,4-Difluorocyclohexyl)-1H-pyrazol-5-amine

The above obtained 3-oxo-3-[trans-4-(trifluoromethyl)cyclohexyl]propanenitrile was solved in 100 ml of ethanol and 4 ml (128.4 mmol) of hydrazine monohydrate was added. Under inert gas atmosphere, the reaction mixture was refluxed for 16 h. The solvent was removed in vacuo. The residue was partitioned between ethyl acetate and water. The combined organic layer was washed with water, dried over anhydrous sodium sulfate, filtered and concentrated in vacuo to yield 6.43 g of the title compound as yellow oil. LC-MS (ESI) m/z 202.2 [MH$^+$]

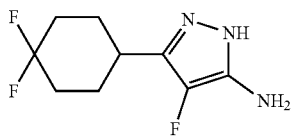

Intermediate 9

3-(4,4-Difluorocyclohexyl)-4-fluoro-1H-pyrazol-5-amine

The title compound was prepared from 4,4-difluorocyclohexane-1-carboxylic acid and fluoroacetonitrile according to the method described in Intermediate 7.

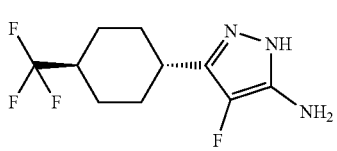

Intermediate 10

4-fluoro-3-[trans-4-(trifluoromethyl)cyclohexyl]-1H-pyrazol-5-amine a) trans-4-(Trifluoromethyl)cyclohexane-1-carbonyl Chloride A mixture of 5 g (25.5 mmol) of trans 4-(trifluoromethyl) cyclohexane-1-carboxylic acid, 100 ml of dichloromethane, 5 ml (68.5 mmol) of thionyl chloride and 0.1 ml of dimethyformamide was refluxed for 6 h. The reaction mixture was concentrated in vacuo and dry tetrahydrofuran was evaporated from the residue several times. The crude product is used in the next step.

b) 2-Fluoro-3-oxo-3-[trans-4-(trifluoromethyl)cyclohexyl]propanenitrile

Under inert gas atmosphere, to a solution of the above obtained trans-4-(trifluoromethyl) cyclohexane-1-carbonyl chloride and 1.5 ml (26.96 mmol) of fluoroacetonitrile in 50 mL of abs. tetrahydrofuran 50 mL (50 mmol) of 1M lithium bis(trimethylsilyl)amide was added dropwise at −78° C. After addition the mixture was stirred at −78° C. for 1 h, then the mixture was allowed to warm to room temperature and poured into 200 mL of water. The pH of the mixture was adjusted to 2 by the addition of 1M hydrochloric acid. The mixture was extracted with ethyl acetate, the combined organic layer was washed with water, dried over anhydrous sodium sulfate, filtered and concentrated in vacuo. The crude product is used in the next step.

c) 4-Fluoro-3-[trans-4-(trifluoromethyl)cyclohexyl]-1H-pyrazol-5-amine

The above obtained 2-fluoro-3-oxo-3-[trans-4-(trifluoromethyl)cyclohexyl]propanenitrile was dissolved in 65 ml of ethanol and 4.4 ml (77 mmol) of hydrazine monohydrate was added. Under inert gas atmosphere, the reaction mixture was refluxed for 16 h. The solvent was removed in vacuo to obtain the title compound as oil. LC-MS (ESI) m/z 252.2 [MH$^+$]

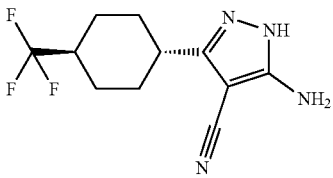

Intermediate 11

5-amino-3-[trans-4-(trifluoromethyl)cyclohexyl]-1H-pyrazole-4-carbonitrile a) 2-[trans-4-(trifluoromethyl)cyclohexanecarbonyl]propanedinitrile To a mixture of 2.7 g (12.58 mmol) trans-4-(trifluoromethyl) cyclohexane-1-carbonyl chloride (Intermediate 10a) and 1.26 g (19.0 mmol) of malononitrile in 15 mL of abs. tetrahydrofuran 1.77 mL (50 mmol) of triethylamine was added dropwise at 0° C. After addition the mixture was stirred at 0° C. for 1 h, then the mixture was allowed to warm to room temperature and poured into 200 mL of water. The mixture was extracted with ethyl acetate, the combined organic layer was washed with water, dried over anhydrous sodium sulfate, filtered and concentrated in vacuo. The crude product is used in the next step.

b) 2-{methoxy[trans-4-(trifluoromethyl)cyclohexyl]methylidene}propanedinitrile

To the above obtained 2-[trans-4-(trifluoromethyl)cyclohexanecarbonyl]propanedinitrile 10 ml of trimethyl orthoformate was added. The reaction mixture was refluxed for 16 h. The reaction mixture was concentrated in vacuo and the residue was chromatographed on silica gel eluting with ethylacetate and cyclohexane (1:1) to yield 1.495 g (46.0%) of the title compound as oil. LC-MS (ESI) m/z 259.1 [MH⁺]

c) 5-amino-3-[trans-4-(trifluoromethyl)cyclohexyl]-1H-pyrazole-4-carbonitrile

The above obtained 2-{methoxy[trans-4-(trifluoromethyl)cyclohexyl]methylidene} propanedinitrile was dissolved in 17 ml of ethanol and 1.4 ml (24.5 mmol) of hydrazine monohydrate was added. The reaction mixture was stirred for 0.5 h at room temperature, diluted with water and extracted with ethylacetate. The combined organic layer was washed with water, dried over anhydrous sodium sulfate, filtered and concentrated in vacuo to yield 1.04 g (69.5%) of the title compound. LC-MS (ESI) m/z 259.2 [MH⁺]

Intermediate 12

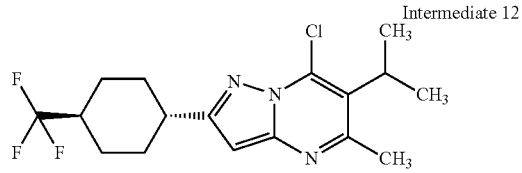

7-Chloro-5-methyl-6-(propan-2-yl)-2-[trans-4-(trifluoromethyl)cyclohexyl]pyrazolo [1,5-a]pyrimidine a) 5-Methyl-6-(propan-2-yl)-2-[trans-4-(trifluoromethyl)cyclohexyl]pyrazolo[1,5-a]pyrimidin-7-ol A mixture of 11.156 g (47.8 mmol) of 3-[trans-4-(trifluoromethyl)cyclohexyl]-1H-pyrazol-5-amine (Intermediate 7), 8 ml (44.6 mmol) of ethyl 2-acetyl-3-methylbutanoate and 0.32 g (1.6 mmol) of p-toluenesulfonic acid monohydrate in 340 mL of toluene was refluxed for 20 h, then cooled to room temperature. The reaction mixture was concentrated in vacuo and the residue was chromatographed on silica gel eluting with dichloromethane and methanol (20:1) to yield 12.4 g (76%) of the title compound. LC-MS (ESI) m/z 342.2 [MH⁺]

b) 7-Chloro-5-methyl-6-(propan-2-yl)-2-[trans-4-(trifluoromethyl)cyclohexyl]-pyrazolo[1,5-a]pyrimidine A mixture of 12.4 g (36.35 mmol) of 5-methyl-6-(propan-2-yl)-2-[trans-4-(trifluoromethyl)cyclohexyl]pyrazolo[1,5-a]pyrimidin-7-ol, 16.7 ml (179 mmol) of phosphorus oxychloride, 12.7 ml (72.9 mmol) of N,N-diisopropylethylamine and 733 ml of toluene was refluxed for 20 h. The reaction mixture was cooled to 20° C., poured into a mixture of sodium hydrogen carbonate solution and ice, then stirred for 2 h. The reaction mixture was filtered, the filtrate was extracted with ethyl acetate, the combined organic layer was washed with water, dried over anhydrous sodium sulfate, filtered and concentrated in vacuo to yield 12.05 g (92%) of the title compound. LC-MS (ESI) m/z 360.2 [MH⁺]

Compounds of Table 4 were prepared from the appropriate acetoacetic ester and 1H-pyrazol-5-amine according to the method described in Intermediate 12.

TABLE 4

| Intermediate | Structure | Intermediate (starting material) | LC-MS (ESI) m/z [MH⁺] |
|---|---|---|---|
| 13 | 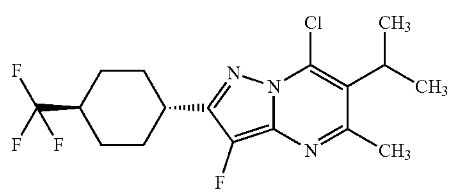 [SMILES: Cc1nc2c(F)c([C@H]3CC[C@H](C(F)(F)F)CC3)nn2c(Cl)c1C(C)C] | 10 | 360.2 |
| 14 | 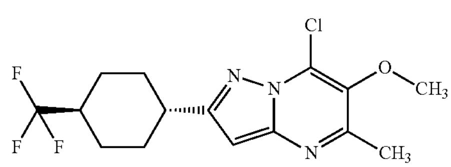 [SMILES: COc1c(C)nc2cc([C@H]3CC[C@H](C(F)(F)F)CC3)nn2c1Cl] | 7 | 348.1 |
| 15 | 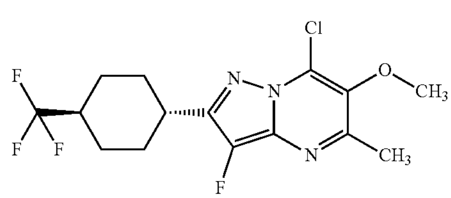 [SMILES: COc1c(C)nc2c(F)c([C@H]3CC[C@H](C(F)(F)F)CC3)nn2c1Cl] | 10 | 366.2 |
| 16 | 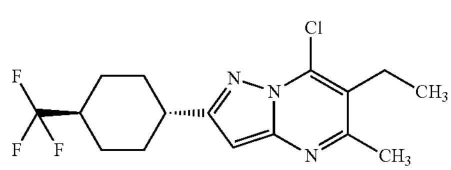 [SMILES: CCc1c(C)nc2cc([C@H]3CC[C@H](C(F)(F)F)CC3)nn2c1Cl] | 7 | 346.1 |

TABLE 4-continued

| Intermediate | Structure | Intermediate (starting material) | LC-MS (ESI) m/z [MH+] |
|---|---|---|---|
| 17 | 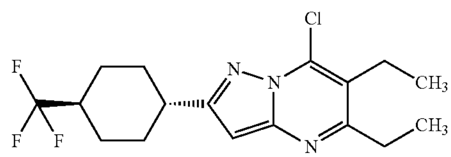 [SMILES: CCc1nc2cc([C@H]3CC[C@H](C(F)(F)F)CC3)nn2c(Cl)c1CC] | 7 | 360.2 |
| 18 | 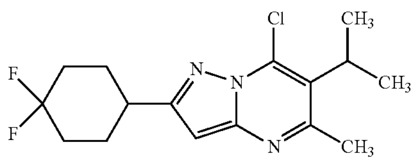 [SMILES: Cc1nc2cc(C3CCC(F)(F)CC3)nn2c(Cl)c1C(C)C] | 8 | 328.2 |
| 19 | 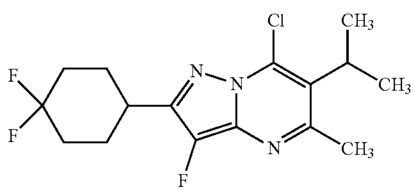 [SMILES: Cc1nc2c(F)c(C3CCC(F)(F)CC3)nn2c(Cl)c1C(C)C] | 9 | 346.2 |
| 20 | 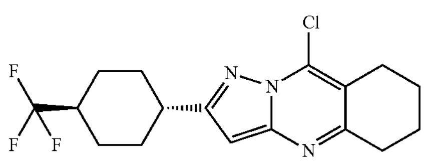 [SMILES: FC(F)(F)[C@H]1CC[C@H](c2cc3nc4c(c(Cl)n3n2)CCCC4)CC1] | 7 | 358.2 |
| 21 | 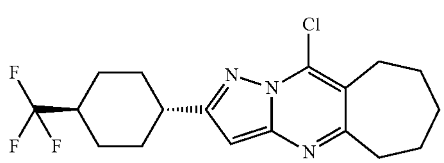 [SMILES: FC(F)(F)[C@H]1CC[C@H](c2cc3nc4c(c(Cl)n3n2)CCCCC4)CC1] | 7 | 372.2 |
| 22 | 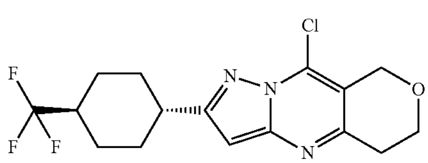 [SMILES: FC(F)(F)[C@H]1CC[C@H](c2cc3nc4c(c(Cl)n3n2)COCC4)CC1] | 7 | 360.2 |
| 23 | 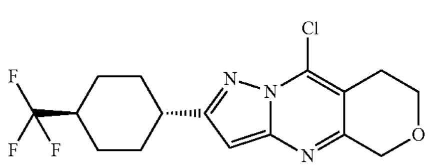 [SMILES: FC(F)(F)[C@H]1CC[C@H](c2cc3nc4c(c(Cl)n3n2)CCOC4)CC1] | 7 | 360.1 |

TABLE 4-continued

| Intermediate | Structure | Intermediate (starting material) | LC-MS (ESI) m/z [MH+] |
|---|---|---|---|
| 24 | 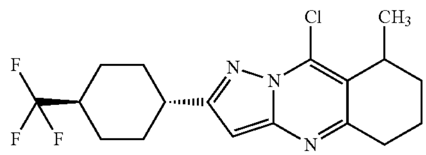 [SMILES: CC1CCCc2nc3cc([C@H]4CC[C@H](C(F)(F)F)CC4)nn3c(Cl)c21] | 7 | 372.2 |
| 25 | 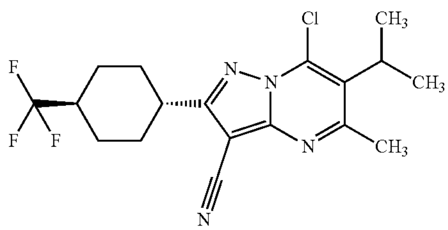 [SMILES: Cc1nc2c(C#N)c([C@H]3CC[C@H](C(F)(F)F)CC3)nn2c(Cl)c1C(C)C] | 11 | 385.2 |
| 26 | 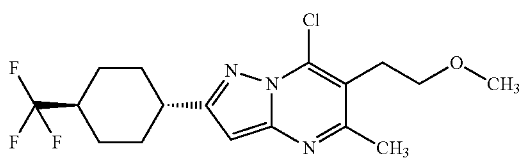 [SMILES: COCCc1c(C)nc2cc([C@H]3CC[C@H](C(F)(F)F)CC3)nn2c1Cl] | 7 | 376.2 |

Route c)

Example 1

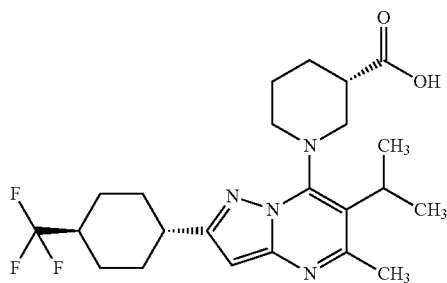

(3S)-1-[5-Methyl-6-(propan-2-yl)-2-[trans-4-(trifluoromethyl)cyclohexyl]pyrazolo[1,5-a]pyrimidin-7-yl]piperidine-3-carboxylic Acid A mixture of 0.8 g (2.22 mmol) of 7-chloro-5-methyl-6-(propan-2-yl)-2-[trans-4-(trifluoromethyl)cyclohexyl]pyrazolo[1,5-a]pyrimidine (Intermediate 12), 0.5 g (3.87 mmol) of S-nipecotic acid and 0.7 ml (4 mmol) of N,N-diisopropylethylamine in 20 mL of N-methyl-pyrrolidone was heated at 130° C. for 20 h, then cooled and diluted with water. The reaction mixture was extracted with ethylacetate, the combined organic layer was washed with water, dried over anhydrous sodium sulphate, filtered and concentrated in vacuo. The residue was chromatographed on silica gel eluting with ethylacetate and cyclohexane (1:2) to yield 0.422 g (42.0%) of the title compound. LC-MS (ESI) m/z 453.2 [MH+]

Route d)

Example 2

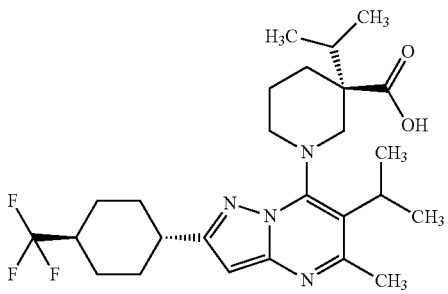

(3S)-1-[5-Methyl-6-(propan-2-yl)-2-[trans-4-(trifluoromethyl)cyclohexyl]-pyrazolo[1,5-a]pyrimidin-7-yl]-3-(propan-2-yl)piperidine-3-carboxylic Acid A mixture of 0.66 g (2.79 mmol) of ethyl (3S)-3-(propan-2-yl)piperidine-3-carboxylate hydrochloride, 0.66 g (5.88 mmol) of potassium tert-butoxide in 15 mL of dimethyl sulfoxide was heated at 100° C. for 16 h. Then 1.0 g (2.77 mmol) 7-chloro-5-methyl-6-(propan-2-yl)-2-[trans-4-(trifluoromethyl)cyclohexyl]pyrazolo[1,5-a]pyrimidine (Intermediate 12) was added to the mixture and heated at 120° C. for 16 h. The reaction mixture was cooled and acidified with acetic acid. The precipitated crystals were filtered off, washed with water. The crude product was chromatographed on silica gel eluting with ethylacetate and cyclohexane (1:2) to yield 0.506 g (36.8%) of the title compound. LC-MS (ESI) m/z 495.3 [MH+]

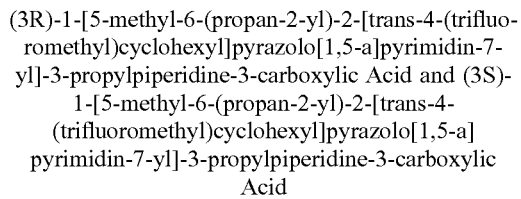

Route e)

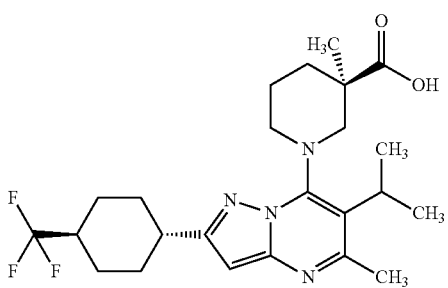

(3R)-3-methyl-1-[5-methyl-6-(propan-2-yl)-2-[trans-4-(trifluoromethyl)cyclohexyl]-pyrazolo [1,5-a]pyrimidin-7-yl]piperidine-3-carboxylic Acid a) Ethyl (3R)-3-methyl-1-[5-methyl-6-(propan-2-yl)-2-[trans-4-(trifluoromethyl) cyclohexyl]pyrazolo[1,5-a]pyrimidin-7-yl]piperidine-3-carboxylate A mixture of 1.0 g (3.06 mmol) of 7-chloro-5-methyl-6-(propan-2-yl)-2-[trans-4-(trifluoromethyl)cyclohexyl]pyrazolo[1,5-a]pyrimidine (Intermediate 12), 0.76 g (4.43 mmol) of ethyl (3R)-3-methylpiperidine-3-carboxylate and 0.8 mL (4.592 mmol) of N,N-diisopropylethylamine in 20 mL of N-methyl-pyrrolidone was heated at 130° C. for 20 h, then cooled and diluted with water. The reaction mixture was extracted with ethylacetate, the combined organic layer was washed with water, dried over anhydrous sodium sulphate, filtered and concentrated in vacuo. The residue was chromatographed on silica gel eluting with toluene and aceton (10:1) to yield 1.44 g (95.3%) of the title compound. LC-MS (ESI) m/z 495.3 [MH+]

b) (3R)-3-methyl-1-[5-methyl-6-(propan-2-yl)-2-[trans-4-(trifluoromethyl)cyclohexyl]pyrazolo [1,5-a]pyrimidin-7-yl]piperidine-3-carboxylic Acid A mixture of 1.443 g (2.91 mmol) of ethyl (3R)-3-methyl-1-[5-methyl-6-(propan-2-yl)-2-[trans-4-(trifluoromethyl)cyclohexyl]pyrazolo[1,5-a]pyrimidin-7-yl]piperidine-3-carboxylate and 5 mL of 20% sodium hydroxide solution in 40 mL of ethanol was refluxed for 5 h, then cooled and acidified with acetic acid. The reaction mixture was extracted with dichloromethane, the combined organic layer was washed with water, dried over anhydrous sodium sulphate, filtered and concentrated in vacuo. The residue was chromatographed on silica gel eluting with ethylacetate and cyclohexane (1:2) to yield 0.934 g (68.6%) of the title compound. LC-MS (ESI) m/z 467.3 [MH+]

Example 4 and Example 5

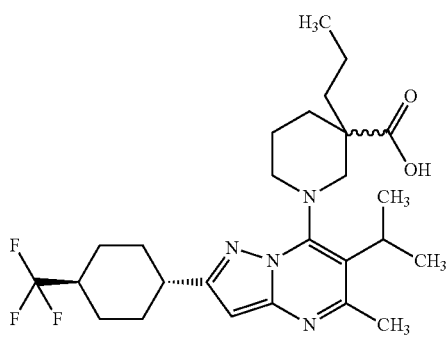

A and B enantiomer (3R)-1-[5-methyl-6-(propan-2-yl)-2-[trans-4-(trifluoromethyl)cyclohexyl]pyrazolo[1,5-a]pyrimidin-7-yl]-3-propylpiperidine-3-carboxylic Acid and (3S)-1-[5-methyl-6-(propan-2-yl)-2-[trans-4-(trifluoromethyl)cyclohexyl]pyrazolo[1,5-a]pyrimidin-7-yl]-3-propylpiperidine-3-carboxylic Acid The racemic form of the title compounds were prepared from 7-chloro-5-methyl-6-(propan-2-yl)-2-[trans-4-(trifluoromethyl)cyclohexyl]pyrazolo[1,5-a]pyrimidine (Intermediate 12), and racem ethyl 3-propylpiperidine-3-carboxylate hydrochloride (Intermediate 4b) according to the methods described in Example 2a and 2b. LC-MS (ESI) m/z 495.3 [MH+]. The A and B enantiomers were separated using chiral preparative HPLC (Kromasil Cellucoat RP 5 μm 150×4.6 mm, F=1 ml/min; eluents: A: H2O+30 mM AmAc B: 80ACN+30 mM AmAc; isocratic 70% B t=25° C.) obtaining enantiomer A (T$_r$ 10.464, Example 4), and enantiomer B (T$_r$ 11.584, Example 5). Their absolute configuration is not determined.

Example 6 and Example 7

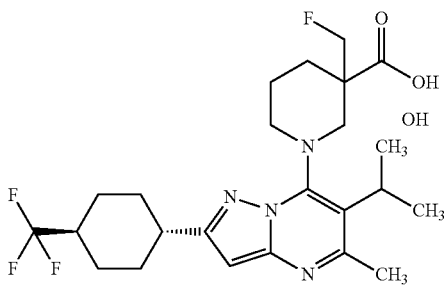

A and B enantiomer (3R)-3-(Fluoromethyl)-1-[5-methyl-6-(propan-2-yl)-2-[trans-4-(trifluoromethyl)cyclohexyl]pyrazolo[1,5-a]pyrimidin-7-yl]piperidine-3-carboxylic Acid and (3S)-3-(Fluoromethyl)-1-[5-methyl-6-(propan-2-yl)-2-[trans-4-(trifluoromethyl)cyclohexyl]pyrazolo[1,5-a]pyrimidin-7-yl]piperidine-3-carboxylic Acid The racemic form of the title compounds were prepared from 7-chloro-5-methyl-6-(propan-2-yl)-2-[trans-4-(trifluoromethyl)cyclohexyl]pyrazolo[1,5-a]pyrimidine (Intermediate 12), and racem Ethyl 3-(fluoromethyl)piperidine-3-carboxylate hydrochloride (Intermediate 5) according to the methods described in Example 2a and 2b. LC-MS (ESI) m/z 485.3 [MH+]. The A and B enantiomers were separated using chiral preparative HPLC (Lux Amylose-1 5 μm 250× 21.1 mm; F=21 ml/min; eluents: n-Heptane:EtOH 80:20+0, 1% TFA t=40° C.) obtaining enantiomer A (Tr 5.9, Example 6), and enantiomer B (Tr 6.7, Example 7). Their absolute configuration is not determined.

Example 8 and Example 9

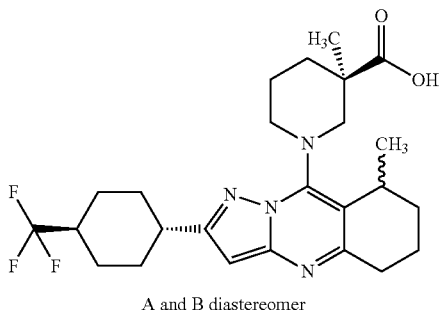

A and B diastereomer (3R)-3-methyl-1-[(8S)-8-methyl-2-[trans-4-(trifluoromethyl)cyclohexyl]-5H,6H,7H,8H-pyrazolo[3,2-b]quinazolin-9-yl]piperidine-3-carboxylic Acid and (3R)-3-methyl-1-[(8R)-8-methyl-2-[trans-4-(trifluoromethyl)cyclohexyl]-5H,6H,7H,8H-pyrazolo[3,2-b]quinazolin-9-yl]piperidine-3-carboxylic Acid a) Ethyl (3R)-3-methyl-1-[(8S)-8-methyl-2-[trans-4-(trifluoromethyl)cyclohexyl]-5H,6H,7H,8H-pyrazolo[3,2-b]quinazolin-9-yl]piperidine-3-carboxylate and Ethyl (3R)-3-methyl-1-[(8R)-8-methyl-2-[trans-4-trifluoromethyl)cyclohexyl]-5H,6H,7H,8H-pyrazolo[3,2-b]quinazolin-9-yl]piperidine-3-carboxylate The racemic form of the title compounds were prepared from racem 9-chloro-8-methyl-2-[trans-4-(trifluoromethyl)cyclohexyl]-5H,6H,7H,8H-pyrazolo[3,2-b]quinazoline (Intermediate 24), and ethyl (3R)-3-methylpiperidine-3-carboxylate hydrochloride according to the methods described in Example 2a. The A and B diastereomer esters were separated using column chromatography on silica gel eluting with dichloromethane-diisopropyl ether 10-1, obtaining diastereomer A ester (TLC in the same system rf=0.5) and diastereomer B ester (TLC in the same system rf=0.45).

b) (3R)-3-Methyl-1-[(8S)-8-methyl-2-[trans-4-(trifluoromethyl)cyclohexyl]-5H,6H,7H,8H-pyrazolo[3,2-b]quinazolin-9-yl]piperidine-3-carboxylic Acid and (3R)-3-Methyl-1-[(8R)-8-methyl-2-[trans-4-(trifluoromethyl)cyclohexyl]-5H,6H,7H,8H-pyrazolo[3,2-b]quinazolin-9-yl]piperidine-3-carboxylic Acid The title compounds were prepared from above diastereomer A ester (Example 8, LC-MS (ESI) m/z 479.2 [MH$^+$]) and diastereomer B ester (Example 9, LC-MS (ESI) m/z 479.2 [MH$^+$]) according to the methods described in Example 2b. Their absolute configuration is not determined.

Examples 10-42 were prepared using analogues methods to those Examples described above and are exemplified below in Table 5.

TABLE 5

| Example | Structure | LC-MS (ESI) m/z [MH$^+$] | Intermediate | Route |
|---|---|---|---|---|
| 10 | 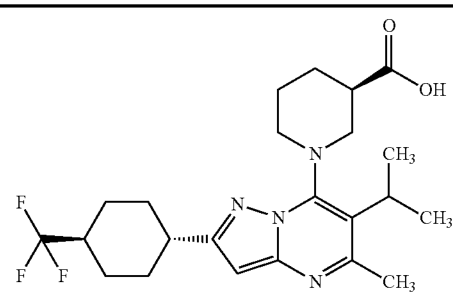 | 453.2 | 12 | c |
| 11 | 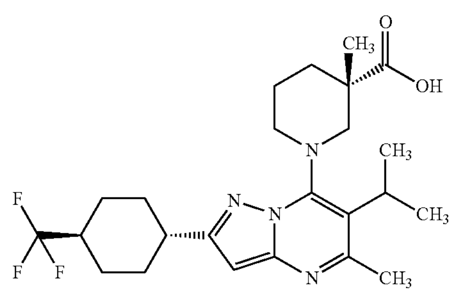 [SMILES: Cc1nc2cc([C@H]3CC[C@H](C(F)(F)F)CC3)nn2c(N2CCC[C@](C)(C(=O)O)C2)c1C(C)C] | 467.3 | 12 | e |
| 12 | 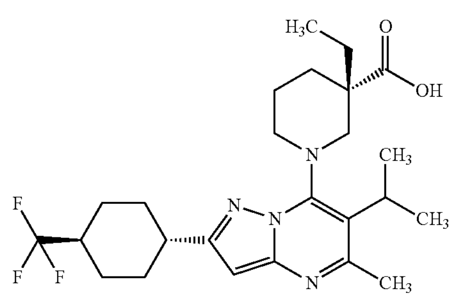 [SMILES: CC[C@]1(C(=O)O)CCCN(c2c(C(C)C)c(C)nc3cc([C@H]4CC[C@H](C(F)(F)F)CC4)nn23)C1] | 481.4 | 12 | e |

TABLE 5-continued
| Example | Structure | LC-MS (ESI) m/z [MH+] | Intermediate | Route |
|---|---|---|---|---|
| 13 | 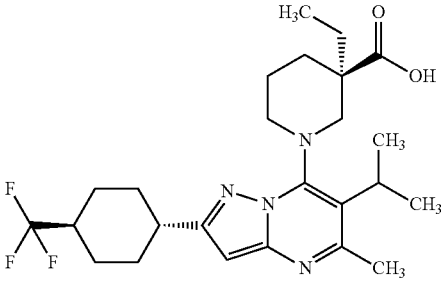 [SMILES: CC[C@@]1(C(=O)O)CCCN(c2c(C(C)C)c(C)nc3cc([C@H]4CC[C@H](C(F)(F)F)CC4)nn23)C1] | 481.4 | 12 | e |
| 14 | 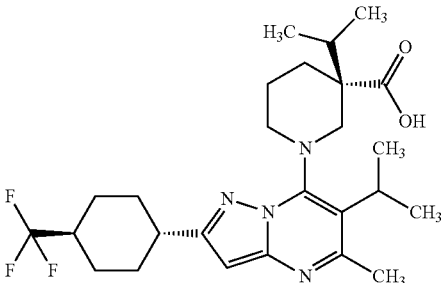 | 495.3 | 12 | d |
| 15 | 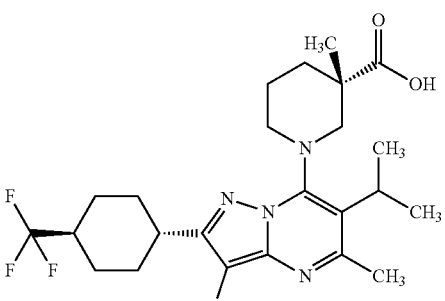 | 485.3 | 13 | e |
| 16 | 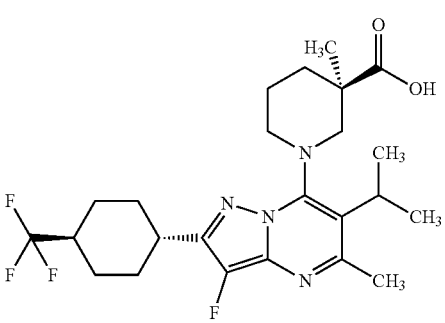 [SMILES: Cc1nc2c(F)c([C@H]3CC[C@H](C(F)(F)F)CC3)nn2c(N2CCC[C@@](C)(C(=O)O)C2)c1C(C)C] | 485.3 | 13 | e |
| 17 | 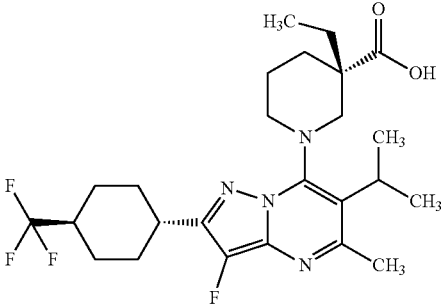 [SMILES: CC[C@]1(C(=O)O)CCCN(c2c(C(C)C)c(C)nc3c(F)c([C@H]4CC[C@H](C(F)(F)F)CC4)nn23)C1] | 499.3 | 13 | e |

TABLE 5-continued

| Example | Structure | LC-MS (ESI) m/z [MH+] | Intermediate | Route |
|---|---|---|---|---|
| 18 | 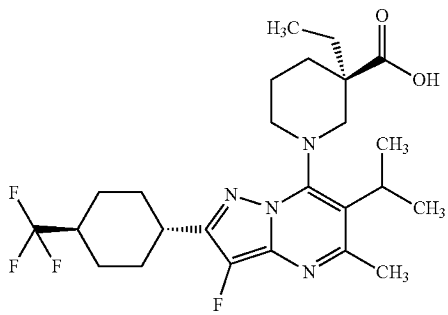 [SMILES: CC[C@@]1(C(=O)O)CCCN(c2c(C(C)C)c(C)nc3c(F)c([C@H]4CC[C@H](C(F)(F)F)CC4)nn23)C1] | 499.3 | 13 | e |
| 19 | 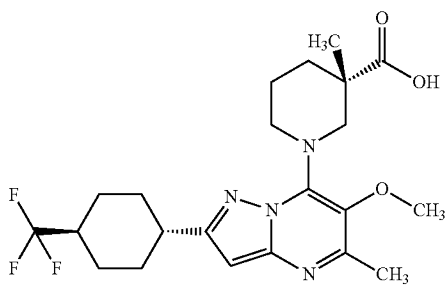 [SMILES: COc1c(C)nc2cc([C@H]3CC[C@H](C(F)(F)F)CC3)nn2c1N1CCC[C@](C)(C(=O)O)C1] | 455.2 | 14 | d |
| 20 | 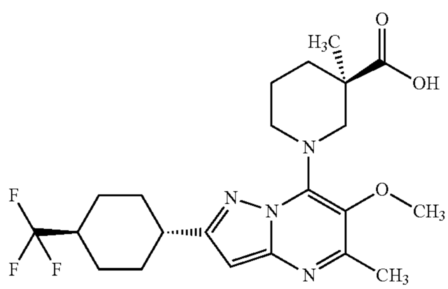 [SMILES: COc1c(C)nc2cc([C@H]3CC[C@H](C(F)(F)F)CC3)nn2c1N1CCC[C@@](C)(C(=O)O)C1] | 455.2 | 14 | d |
| 21 | 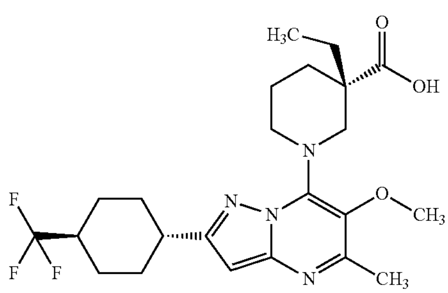 [SMILES: CC[C@]1(C(=O)O)CCCN(c2c(OC)c(C)nc3cc([C@H]4CC[C@H](C(F)(F)F)CC4)nn23)C1] | 469.2 | 14 | d |
| 22 | 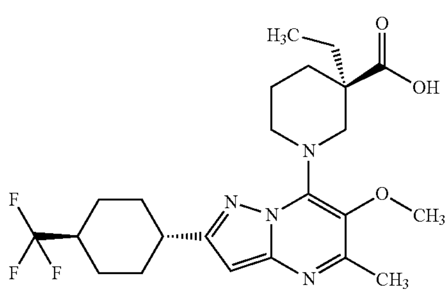 [SMILES: CC[C@@]1(C(=O)O)CCCN(c2c(OC)c(C)nc3cc([C@H]4CC[C@H](C(F)(F)F)CC4)nn23)C1] | 469.2 | 14 | d |

TABLE 5-continued

| Example | Structure | LC-MS (ESI) m/z [MH+] | Intermediate | Route |
|---|---|---|---|---|
| 23 | 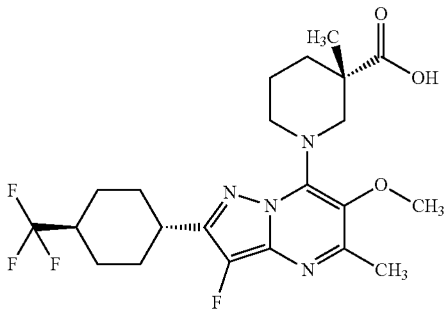 [SMILES: COc1c(C)nc2c(F)c([C@H]3CC[C@H](C(F)(F)F)CC3)nn2c1N1CCC[C@](C)(C(=O)O)C1] | 473.2 | 15 | e |
| 24 | 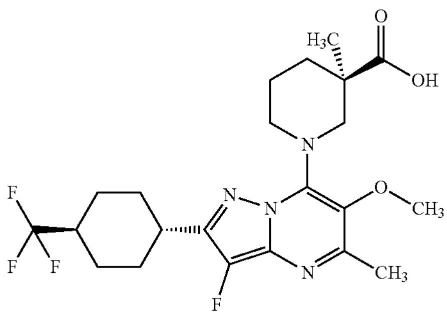 [SMILES: COc1c(C)nc2c(F)c([C@H]3CC[C@H](C(F)(F)F)CC3)nn2c1N1CCC[C@@](C)(C(=O)O)C1] | 473.2 | 15 | e |
| 25 | 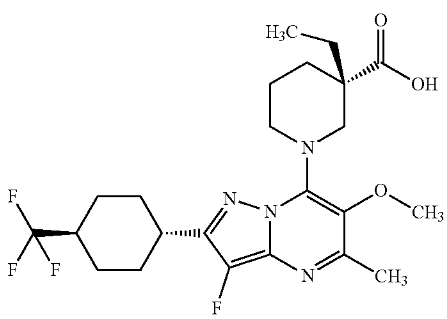 [SMILES: CC[C@]1(C(=O)O)CCCN(c2c(OC)c(C)nc3c(F)c([C@H]4CC[C@H](C(F)(F)F)CC4)nn23)C1] | 487.2 | 15 | d |
| 26 | 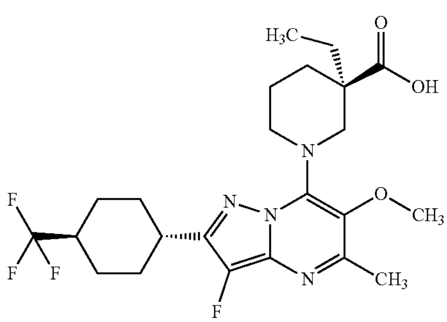 [SMILES: CC[C@@]1(C(=O)O)CCCN(c2c(OC)c(C)nc3c(F)c([C@H]4CC[C@H](C(F)(F)F)CC4)nn23)C1] | 487.2 | 15 | e |
| 27 | 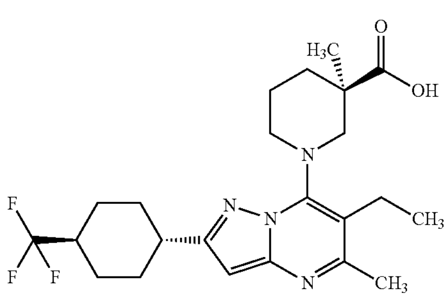 [SMILES: CCc1c(C)nc2cc([C@H]3CC[C@H](C(F)(F)F)CC3)nn2c1N1CCC[C@@](C)(C(=O)O)C1] | 453.2 | 16 | d |

TABLE 5-continued

| Example | Structure | LC-MS (ESI) m/z [MH+] | Intermediate | Route |
|---|---|---|---|---|
| 28 | 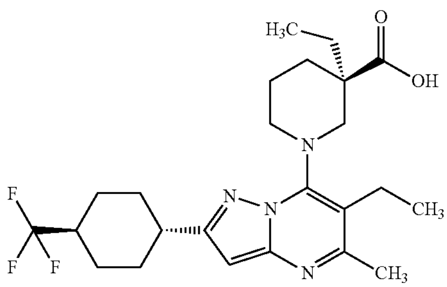 [SMILES: CCc1c(C)nc2cc([C@H]3CC[C@H](C(F)(F)F)CC3)nn2c1N1CCC[C@@](CC)(C(=O)O)C1] | 467.3 | 16 | d |
| 29 | 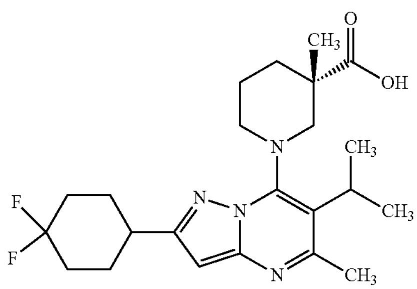 [SMILES: Cc1nc2cc(C3CCC(F)(F)CC3)nn2c(N2CCC[C@](C)(C(=O)O)C2)c1C(C)C] | 435.2 | 18 | e |
| 30 | 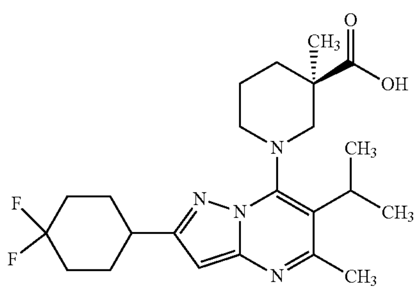 [SMILES: Cc1nc2cc(C3CCC(F)(F)CC3)nn2c(N2CCC[C@@](C)(C(=O)O)C2)c1C(C)C] | 435.2 | 18 | e |
| 31 | 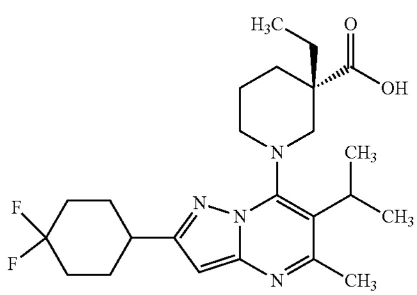 [SMILES: CC[C@]1(C(=O)O)CCCN(c2c(C(C)C)c(C)nc3cc(C4CCC(F)(F)CC4)nn23)C1] | 449.3 | 18 | e |
| 32 | 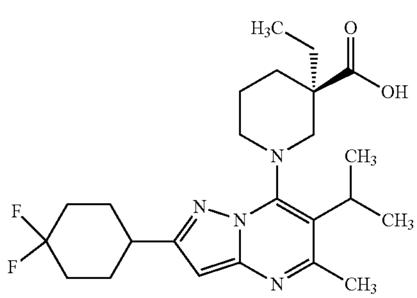 [SMILES: CC[C@@]1(C(=O)O)CCCN(c2c(C(C)C)c(C)nc3cc(C4CCC(F)(F)CC4)nn23)C1] | 449.3 | 18 | e |

TABLE 5-continued

| Example | Structure | LC-MS (ESI) m/z [MH+] | Intermediate | Route |
|---|---|---|---|---|
| 33 | 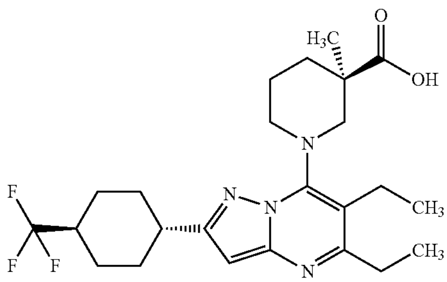 [SMILES: CCc1nc2cc([C@H]3CC[C@H](C(F)(F)F)CC3)nn2c(N2CCC[C@@](C)(C(=O)O)C2)c1CC] | 467.3 | 17 | e |
| 34 | 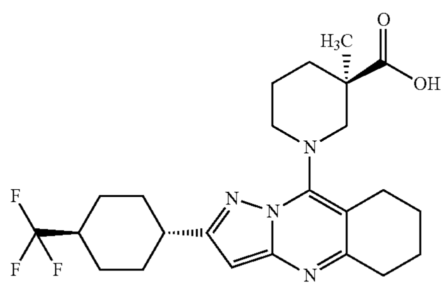 [SMILES: C[C@@]1(C(=O)O)CCCN(c2c3c(nc4cc([C@H]5CC[C@H](C(F)(F)F)CC5)nn24)CCCC3)C1] | 465.2 | 20 | e |
| 35 | 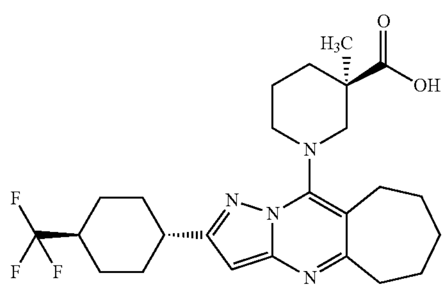 [SMILES: C[C@@]1(C(=O)O)CCCN(c2c3c(nc4cc([C@H]5CC[C@H](C(F)(F)F)CC5)nn24)CCCCC3)C1] | 479.2 | 21 | e |
| 36 | 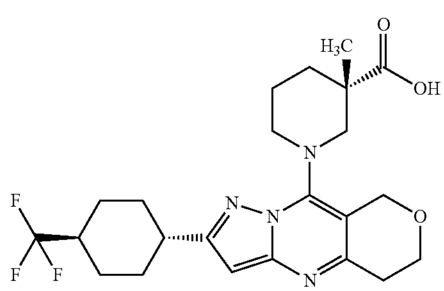 [SMILES: C[C@]1(C(=O)O)CCCN(c2c3c(nc4cc([C@H]5CC[C@H](C(F)(F)F)CC5)nn24)CCOC3)C1] | 467.2 | 22 | e |
| 37 | 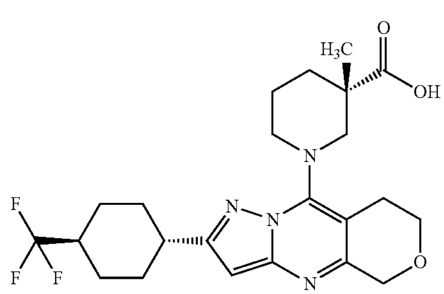 [SMILES: C[C@]1(C(=O)O)CCCN(c2c3c(nc4cc([C@H]5CC[C@H](C(F)(F)F)CC5)nn24)COCC3)C1] | 467.2 | 23 | e |

TABLE 5-continued

| Example | Structure | LC-MS (ESI) m/z [MH+] | Intermediate | Route |
|---|---|---|---|---|
| 38 | 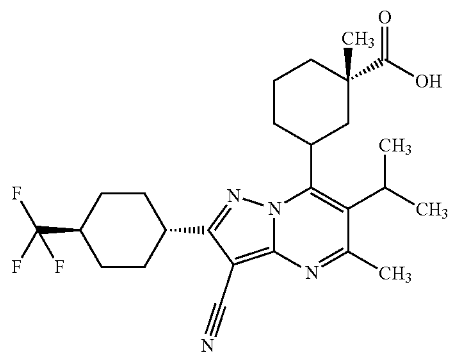 [SMILES: Cc1nc2c(C#N)c([C@H]3CC[C@H](C(F)(F)F)CC3)nn2c(C2CCC[C@](C)(C(=O)O)C2)c1C(C)C] | 492.3 | 25 | e |
| 39 | 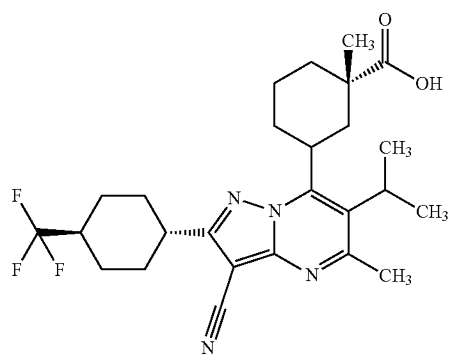 [SMILES: Cc1nc2c(C#N)c([C@H]3CC[C@H](C(F)(F)F)CC3)nn2c(C2CCC[C@](C)(C(=O)O)C2)c1C(C)C] | 492.3 | 25 | e |
| 40 | 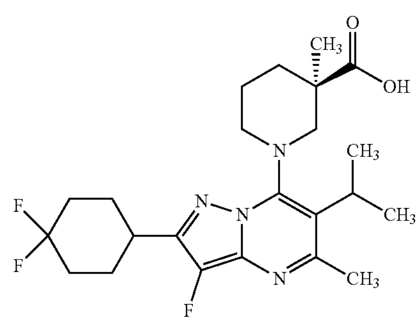 [SMILES: Cc1nc2c(F)c(C3CCC(F)(F)CC3)nn2c(N2CCC[C@@](C)(C(=O)O)C2)c1C(C)C] | 453.2 | 18 | e |
| 41 | 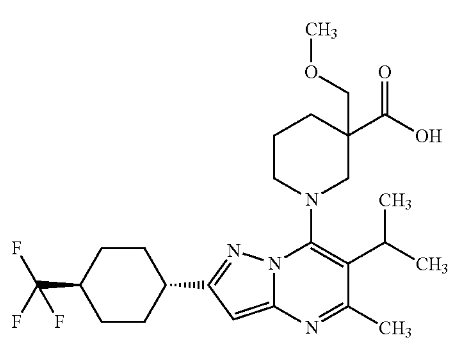 [SMILES: COCC1(C(=O)O)CCCN(c2c(C(C)C)c(C)nc3cc([C@H]4CC[C@H](C(F)(F)F)CC4)nn23)C1] | 497.2 | 12 | e |

TABLE 5-continued

| Example | Structure | LC-MS (ESI) m/z [MH+] | Intermediate | Route |
|---|---|---|---|---|
| 42 | 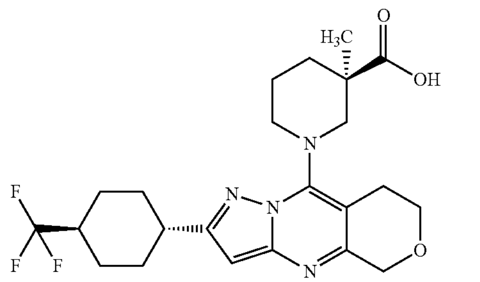 [SMILES: C[C@@]1(C(=O)O)CCCN(c2c3c(nc4cc([C@H]5CC[C@H](C(F)(F)F)CC5)nn24)COCC3)C1] | 467.2 | 23 | e |
| 43 | 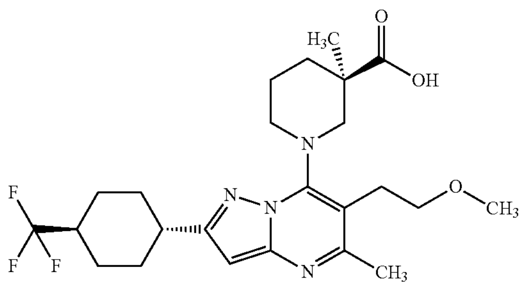 [SMILES: COCCc1c(C)nc2cc([C@H]3CC[C@H](C(F)(F)F)CC3)nn2c1N1CCC[C@@](C)(C(=O)O)C1] | 483.3 | 26 | e |

Preparation of Pharmaceutical Compositions

The following formulation examples illustrate representative pharmaceutical compositions of this invention. The present invention however is not limited to the following pharmaceutical compositions.

A) Solid Oral Dosage Forms

I., Tablets

| | |
|---|---|
| Active ingredient(s) | 0.01-90% |
| Filler | 1-99.9% |
| Binder | 0-20% |
| Disintegrant | 0-20% |
| Lubricant | 0-10% |
| Other specific excipient(s) | 0-50% |

II., Orodispersible Films

| | |
|---|---|
| Active ingredient(s) | 0.01-90% |
| Film forming agent | 1-99.9% |
| Plasticizer | 0-40% |
| Other specific excipient(s) | 0-50% |

B) Liquid Oral Dosage Forms

III., Oral Suspensions

| | |
|---|---|
| Active ingredient(s) | 0.01-50% |
| Liquid vehicle | 10-99.9% |
| Wetting agent | 0-50% |
| Thickener | 0-50% |
| Buffering agent | q.s. |
| Osmotic agent | 0-50% |
| Preservatives | q.s. |

IV., Syrups

| | |
|---|---|
| Active ingredient(s) | 0.01-50% |
| Solvent | 10-99.9% |
| Sugar component | 1-20% |
| Flavouring agents | 0-10% |

C) Parenteral Dosage Forms

V., Intravenous Injections

| | |
|---|---|
| Active ingredient(s) | 0.01-50% |
| Solvent | 10-99.9% |
| Co-solvent | 0-99.9% |
| Osmotic agent | 0-50% |
| Buffering agent | q.s. |

D) Other Dosage Forms

VI., Suppositories

| | |
|---|---|
| Active ingredient(s) | 0.01-50% |
| Suppository base | 1-99.9% |
| Surface-active agents | 0-20% |
| Lubricants | 0-20% |
| Preservatives | q.s. |

VII., Eye Drops

| | |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Buffering agent | q.s. |
| Preservatives | q.s. |

The invention claimed is:

1. A compound of formula (I) wherein:

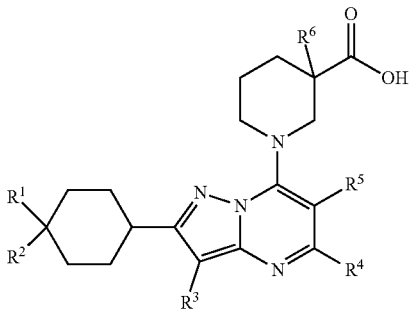

(I)

R$^1$ and R$^2$ are independently selected from hydrogen, halogen atom, C$_{1-6}$alkyl, or haloC$_{1-6}$alkyl;
R$^3$ is hydrogen, halogen atom, C$_{1-6}$alkyl, or cyano group;
R$^4$ is C$_{1-6}$alkyl;
R$^5$ is C$_{1-6}$alkyl optionally substituted by a halogen atom, halogen atoms, C$_{3-5}$ cycloalkyl; C$_{3-5}$ cycloalkylC$_{1-6}$alkyl, dialkylamino, C$_{1-6}$alkoxy, C$_{1-6}$alkoxyC$_{1-6}$alkyl, C$_{1-6}$alkylthio group, tetrahydrofuranyl, tetrahydrofuranylC$_{1-6}$alkyl, tetrahydropyranyl, or tetrahydropyranylC$_{1-6}$alkyl;
or R$_4$ and R$_5$ together form a 3 to 7-membered saturated ring, wherein the 3 to 7-membered saturated ring is unsubstituted or substituted by one or more C$_{1-3}$alkyl, C$_{1-3}$alkoxy, haloC$_{1-3}$alkyl, or C$_{1-3}$alkylcarbonyl, and wherein the members of the ring are selected from the group consisting of carbon, nitrogen, oxygen, and sulphur;
R$^6$ is hydrogen, halogen atom, C$_{1-6}$alkyl, hydroxyl, C$_{1-6}$alkoxy, C$_{1-6}$alkoxyC$_{1-6}$alkyl, haloC$_{1-6}$alkyl, or an amino group; or pharmaceutically acceptable salts, hydrolysable esters, racemates, enantiomers, diastereomers, solvates and hydrates thereof.

2. A compound according to claim 1 wherein R$^1$ and R$^2$ are independently selected from hydrogen, halogen atom, C$_{1-6}$alkyl, or haloC$_{1-6}$alkyl;
R$^3$ is hydrogen, halogen atom, C$_{1-6}$alkyl, or cyano group;
R$^4$ is C$_{1-6}$alkyl;
R$^5$ is C$_{1-6}$alkyl optionally substituted by a halogen atom, halogen atoms, C$_{3-5}$ cycloalkyl, C$_{3-5}$ cycloalkylC$_{1-6}$alkyl, dialkylamino, C$_{1-6}$alkoxy, C$_{1-6}$alkoxyC$_{1-6}$alkyl, C$_{1-6}$alkylthio group, tetrahydrofuranyl, tetrahydrofuranylC$_{1-6}$alkyl, tetrahydropyranyl, or tetrahydropyranylC$_{1-6}$alkyl;
R$^6$ is hydrogen, halogen atom, C$_{1-6}$alkyl, hydroxyl, C$_{1-6}$alkoxy, C$_{1-6}$alkoxyC$_{1-6}$alkyl, haloC$_{1-6}$alkyl, or an amino group; or pharmaceutically acceptable salts, hydrolysable esters, racemates, enantiomers, diastereomers, solvates and hydrates thereof.

3. A compound according to claim 1 wherein
R$^1$ and R$^2$ are independently selected from hydrogen, halogen atom, C$_{1-6}$alkyl, or haloC$_{1-6}$alkyl;
R$^3$ is hydrogen, halogen atom, C$_{1-6}$alkyl, or cyano group;
R$_4$ and R$_5$ together form a 3 to 7-membered saturated ring, wherein the 3 to 7-membered saturated ring is unsubstituted or substituted by one or more C$_{1-3}$alkyl, C$_{1-3}$alkoxy, haloC$_{1-3}$alkyl, or C$_{1-3}$alkylcarbonyl, and wherein the members of the ring are selected from the group consisting of carbon, nitrogen, oxygen, and sulphur;
R$^6$ is hydrogen, halogen atom, C$_{1-6}$alkyl, hydroxyl, C$_{1-6}$alkoxy, C$_{1-6}$alkoxyC$_{1-6}$alkyl, haloC$_{1-6}$alkyl, or an amino group; or pharmaceutically acceptable salts, hydrolysable esters, racemates, enantiomers, diastereomers, solvates and hydrates thereof.

4. A compound according to claim 1 wherein R$^4$ is methyl; and R$^5$ is isopropyl or C$_{1-6}$alkoxyC$_{1-6}$alkyl.

5. A compound according to claim 1 selected from the group consisting of
(3S)-1[5-Methyl-6-(propan-2-yl)-2-[trans-4-(trifluoromethyl)cyclohexyl]pyrazolo[1,5-a]pyrimidin-7-yl]piperidine-3-carboxylic acid;
(3S)-1[5-Methyl-6-(propan-2-yl)-2-[trans-4-(trifluoromethyl)cyclohexyl]pyrazolo[1,5-a]pyrimidin-7-yl]-3-(propan-2-yl)piperidine-3-carboxylic acid;
(3R)-3-Methyl-1-[5-methyl-6-(propan-2-yl)-2-[trans-4-(trifluoromethyl)cyclohexyl]pyrazolo[1,5-a]pyrimidin-7-yl]piperidine-3-carboxylic acid;
(3R)-1-[5-Methyl-6-(propan-2-yl)-2-[trans-4-(trifluoromethyl)cyclohexyl]pyrazolo [1,5-a]pyrimidin-7-yl]-3-propylpiperidine-3-carboxylic acid;
(3S)-1-[5-Methyl-6-(propan-2-yl)-2-[trans-4-(trifluoromethyl)cyclohexyl]pyrazolo[1,5-a]pyrimidin-7-yl]-3-propylpiperidine-3-carboxylic acid;
(3R)-3-(Fluoromethyl)-1-[5-methyl-6-(propan-2-yl)-2-[trans-4-(trifluoromethyl) cyclohexyl]pyrazolo[1,5-a]pyrimidin-7-yl]piperidine-3-carboxylic acid;
(3S)-3-(Fluoromethyl)-1-[5-methyl-6-(propan-2-yl)-2-[trans-4-(trifluoromethyl) cyclohexyl]pyrazolo[1,5-a]pyrimidin-7-yl]piperidine-3-carboxylic acid;
(3R)-3-Methyl-1-[(8S)-8-methyl-2-[trans-4-(trifluoromethyl)cyclohexyl]-5H,6H,7H,8H-pyrazolo[3, 2-b]quinazolin-9-yl]piperidine-3-carboxylic acid;
(3R)-3-Methyl-1-[(8R)-8-methyl-2-[trans-4-(trifluoromethyl)cyclohexyl]-5H,6H,7H,8H-pyrazolo[3, 2-b]quinazolin-9-yl]piperidine-3-carboxylic acid;
(3R)-1-[5-Methyl-6-(propan-2-yl)-2-[trans-4-(trifluoromethyl)cyclohexyl]pyrazolo [1,5-a]pyrimidin-7-yl]piperidine-3-carboxylic acid;
(3S)-3-Methyl-1-[5-methyl-6-(propan-2-yl)-2-[trans-4-(trifluoromethyl)cyclohexyl]pyrazolo[1,5-a]pyrimidin-7-yl]piperidine-3-carboxylic acid;
(3S)-3-Ethyl-1-[5-methyl-6-(propan-2-yl)-2-[trans-4-(trifluoromethyl)cyclohexyl]pyrazolo[1,5-a]pyrimidin-7-yl]piperidine-3-carboxylic acid;
(3R)-3-Ethyl-1-[5-methyl-6-(propan-2-yl)-2-[trans-4-(trifluoromethyl)cyclohexyl]pyrazolo[1,5-a]pyrimidin-7-yl]piperidine-3-carboxylic acid;
(3R)-1-[5-Methyl-6-(propan-2-yl)-2-[trans-4-(trifluoromethyl)cyclohexyl]pyrazolo [1,5-a]pyrimidin-7-yl]-3-(propan-2-yl)piperidine-3-carboxylic acid;
(3S)-1-[3-Fluoro-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid;
(3R)-1-[3-Fluoro-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid;
(3S)-3-Ethyl-1-[3-fluoro-5-methyl-6-(propan-2-yl)-2-[trans-4-(trifluoromethyl) cyclohexyl]pyrazolo[1,5-a]pyrimidin-7-yl]piperidine-3-carboxylic acid;
(3R)-3-Ethyl-1-[3-fluoro-5-methyl-6-(propan-2-yl)-2-[trans-4-(trifluoromethyl) cyclohexyl]pyrazolo[1,5-a]pyrimidin-7-yl]piperidine-3-carboxylic acid;
(3S)- 1-{3-Fluoro-6-methoxy-5-methyl-2-[trans-4-(trifluoromethyl)cyclohexyl]pyrazolo[1,5-a]pyrimidin-7-yl}-3-methylpiperidine-3-carboxylic acid;

(3R)-1-{3-Fluoro-6-methoxy-5-methyl-2-[trans-4-(trifluoromethyl)cyclohexyl]pyrazolo[1,5-a]pyrimidin-7-yl}-3-methylpiperidine-3-carboxylic acid;
(3S)-3-Ethyl-1-{6-methoxy-5-methyl-2-[trans-4-(trifluoromethyl)cyclohexyl]pyrazolo[1,5-a]pyrimidin-7-yl}piperidine-3-carboxylic acid;
(3R)-3-Ethyl-1-{6-methoxy-5-methyl-2-[trans-4-(trifluoromethyl)cyclohexyl]pyrazolo[1,5-a]pyrimidin-7-yl}piperidine-3-carboxylic acid;
(3S)-1-{3-Fluoro-6-methoxy-5-methyl-2-[trans-4-(trifluoromethyl)cyclohexyl]pyrazolo[1,5-a]pyrimidin-7-yl}-3-methylpiperidine-3-carboxylic acid;
(3R)-1-{3-Fluoro-6-methoxy-5-methyl-2-[trans-4-(trifluoromethyl)cydohexyl]pyrazolo[1,5-a]pyrimidin-7-yl}-3-methylpiperidine-3-carboxylic acid;
(3S)-3-Ethyl-1-{3-fluoro-6-methoxy-5-methyl-2-[trans-4-(trifluoromethyl) cydohexyl]pyrazolo[1,5-a]pyrimidin-7-yl}piperidine-3-carboxylic acid;
(3R)-3-Ethyl-1-{3-fluoro-6-methoxy-5-methyl-2-[trans-4-(trifluoromethyl) cyclohexyl]pyrazolo[1,5-a]pyrimidin-7-yl}piperidine-3-carboxylic acid;
(3R)-1-{6-Ethyl-5-methyl-2-[trans-4-(trifluoromethyl) cyclohexyl]pyrazolo[1,5-a]pyrimidin-7-yl}-3-methylpiperidine-3-carboxylic acid;
(3R)-3-Ethyl-1-{6-ethyl-5-methyl-2-[trans-4-(trifluoromethyl)cyclohexyl]pyrazolo [1,5-a]pyrimidin-7-yl}piperidine-3-carboxylic acid;
(3S)-1-[2-(4,4-Difluorocydohexyl)-5-methyl-6-(propan-2-yl)pyrazolo[1,5-a]pyrimidin-7-yl]-3-methylpiperidine-3-carboxylic acid;
(3R)-1-[2-(4,4-Difluorocyclohexyl)-5-methyl-6-(propan-2-yl)pyrazolo[1,5-a]pyrimidin-7-yl]-3-methylpiperidine-3-carboxylic acid;
(3S)-1-[2-(4,4-Difluorocydohexyl)-5-methyl-6-(propan-2-yl)pyrazolo[1,5-a]pyrimidin-7-yl]-3-ethylpiperidine-3-carboxylic acid;
(3R)-1-[2-(4,4-Difluorocyclohexyl)-5-methyl-6-(propan-2-yl)pyrazolo[1,5-a]pyrimidin-7-yl]-3-ethylpiperidine-3-carboxylic acid;
(3R)-1-[2-(4,4-Difluorocydohexyl)-5,6-diethylpyrazolo[1,5-a]pyrimidin-7-yl]-3-methylpiperidine-3-carboxylic acid;
(3R)-3-Methyl-1-{2-[trans-4-(trifluoromethyl)cyclohexyl]-5H,6H,7H,8H-pyrazolo [3,2-b]quinazolin-9-yl}piperidine-3-carboxylic acid;
(3R)-3-Methyl-1-{5-[trans-4-(trifluoromethyl)cyclohexyl]-2,6,7-triazatricyclo[7.5.0.0$^{3,7}$]tetradeca-1,3,5,8-tetraen-8-yl}piperidine-3-carboxylic acid;
(3R)-3-Methyl-1-{5-[(trans)-4-(trifluoromethyl)cyclohexyl]-11-oxa-2,6,7-triazatricyclo[7.4.0.0$^{3,7}$]trideca-1,3,5,8-tetraen-8-yl}piperidine-3-carboxylic acid;
(3S)-3-Methyl-1-{5-[trans-4-(trifluoromethyl)cyclohexyl]-12-oxa-2,6,7-triazatricyclo [7.4.0.0$^{3,7}$]trideca-1,3,5,8-tetraen-8-yl}piperidine-3-carboxylic acid;
(3S)-1-[3-Cyano-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid;
(3R)-1-[3-Cyano-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid;
(3R)-1-[2-(4,4-Difluorocydohexyl)-3-fluoro-5-methyl-6-(propan-2-yl)pyrazolo[1, 5-a]pyrimidin-7-yl]-3-methylpiperidine-3-carboxylic acid; and
(3R)-1-[6-(2-methoxyethyl)-5-methyl-2-[trans-4-(trifluoromethyl)cyclohexyl]pyrazolo[1,5-a]pyrimidin-7-yl]-3-methylpiperidine-3-carboxylic acid.

6. A process for preparing the compounds of formula (I) according to claim 1 characterized by
step 1) reacting a carboxylic acid ester of formula (II) or carboxylic acid chloride of formula (III)

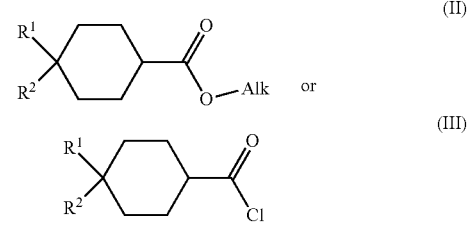

with an acetonitrile of formula (IV)

then
step 2) reacting the obtained acylacetonitrile of formula (V)

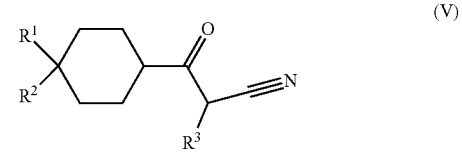

2a) with hydrazine hydrate to provide a compound of formula (VI)

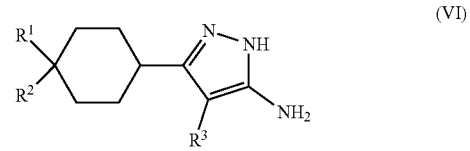

wherein $R^3$ is hydrogen, halogen atom, or $C_{1-6}$alkyl group; or
2b) with trimethyl orthoformate to provide the malononitrile of formula (XIV)

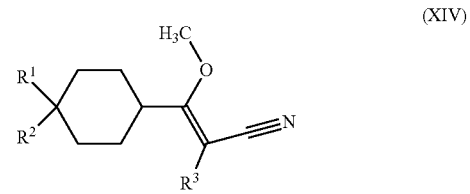

wherein $R^3$ is a cyano group; which is then reacted with hydrazine hydrate to provide a compound of formula (VI)

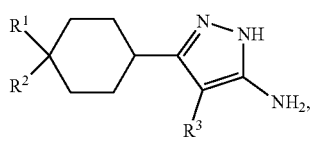
(VI)

then step 3) the compound of formula (VI) is reacted with an acylacetic ester of formula (VII)

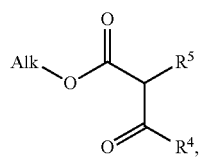
(VII)

then step 4) chlorinating the obtained compound of formula (VIII)

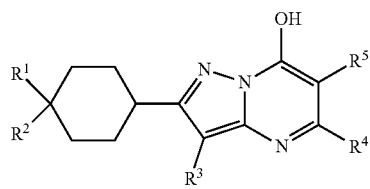
(VIII)

to obtain a chloro compound of formula (IX)

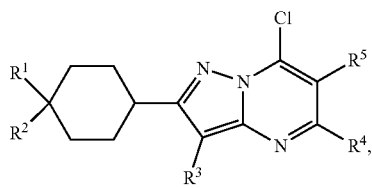
(IX)

and step 5) reacting the chloro compound of formula (IX) with either 5c) a nipecotic acid of formula (X)

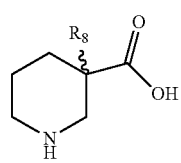
(X)

, or 5d) an alkali salt of formula (XI)

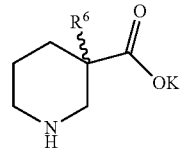
(XI)

, wherein K is an alkali metal, or 5e) a nipecotic acid ester of formula (XII)

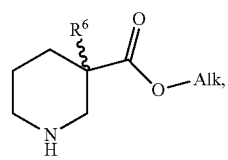
(XII)

wherein Alk is an alkyl group, to provide the ester of formula (XIII)

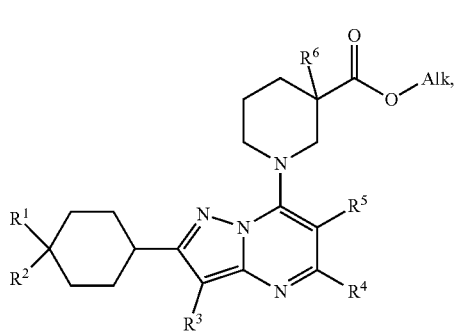
(XIII)

and saponifying the ester of formula (XIII) with a strong base or hydrolyzing the ester of formula (XIII) with a strong acid.

7. A pharmaceutical composition comprising a therapeutically effective amount of a compound of formula (I) or pharmaceutically acceptable salts, hydrolysable esters, racemates, enantiomers, diastereomers, solvates and hydrates thereof according to claim 1 as active ingredient and a pharmaceutically acceptable carrier.

8. A combination comprising a compound of formula (I) or pharmaceutically acceptable salts, hydrolysable esters, racemates, enantiomers, diastereomers, solvates and hydrates thereof according to claim 1 and one or more therapeutically active co-agents.

9. A process for manufacturing a pharmaceutical composition having $GABA_B$ receptor positive allosteric modulator effect characterized by mixing a compound of formula (I) or pharmaceutically acceptable salts, hydrolysable esters, racemates, enantiomers, diastereomers, solvates and hydrates thereof according to claim 1, or optical antipodes or racemates and/or salts thereof, as active ingredients with pharmaceutically acceptable excipients.

10. A method for positive allosteric modulation of the $GABA_B$ receptor in a subject suffering from a disorder which requires positive allosteric modulation of the $GABA_B$ receptor characterized by administering to the subject an effective amount of a compound of formula (I) as claimed in claim 1, or optical antipodes or racemates and/or salts thereof.

11. The method according to claim 10 wherein the disorder is selected from the group of psychiatric disorders, neurodevelopmental disorders, cognitive disorders, epilepsy, spasticity, skeletal muscle rigidity, spinal cord injury, multiple sclerosis, amyotrophic lateral sclerosis, cerebral palsy, essential tremor, pain, substance abuse, obesity, binge eating, asthma, cough, urinary incontinence, gastroesophageal reflux disease, transient lower esophageal sphincter relaxation, and irritable bowel syndrome.

12. The method of claim 10, wherein the compound of formula (I) is combined with pharmaceutically acceptable excipients.

13. The method of claim 11, wherein the psychiatric disorder is selected from anxiety, panic disorder, posttraumatic disorder, depression, and schizophrenia.

14. The method of claim 11, wherein the neurodevelopmental disorder is selected from autism spectrum disorder, obsessive-compulsive disorder, and Fragile X syndrome.

15. The method of claim 11, wherein the pain is selected from neuropathic, visceral, and osteoarthritic pain.

16. The method of claim 14, wherein the neurodevelopmental disorder is autism spectrum disorder.

17. The process of claim 6, wherein reacting the carboxylic acid ester derivative of formula (II) or carboxylic acid chloride derivative of formula (III) with an acetonitrile derivative of formula (IV) is carried out in the presence of a strong base.

18. The process of claim 6, wherein the compound of formula (VI) is reacted with the acylacetic ester derivative of formula (VII) under heat.

19. The process of claim 6, wherein the compound of formula (VIII) is chlorinated under heat.

20. A compound according to claim 5 selected from the group consisting of
(3R)-3-Methyl-1-[5-methyl-6-(propan-2-yl)-2-[trans-4-(trifluoromethyl)cyclohexyl]pyrazolo[1,5-a]pyrimidin-7-yl]piperidine-3-carboxylic acid;
(3S)-3-(Fluoromethyl)-1-[5-methyl-6-(propan-2-yl)-2-[trans-4-(trifluoromethyl) cyclohexyl]pyrazolo[1,5-a]pyrimidin-7-yl]piperidine-3-carboxylic acid;
(3R)-3-Ethyl-1-[5-methyl-6-(propan-2-yl)-2- [trans-4-(trifluoromethyl)cyclohexyl]pyrazolo[1,5-a]pyrimidin-7-yl]piperidine-3-carboxylic acid;
(3R)-1-[3-Fluoro-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid; and
(3R)-3-Ethyl-1-[3-fluoro-5-methyl-6-(propan-2-yl)-2-[trans-4-(trifluoromethyl) cyclohexyl]pyrazolo[1,5-a]pyrimidin-7-yl]piperidine-3-carboxylic acid.

21. A compound according to claim 5 selected from the group consisting of
(3S)-1-[5-Methyl-6-(propan-2-yl)-2-[trans-4-(trifluoromethyl)cyclohexyl]pyrazolo[1,5-a]pyrimidin-7-yl]piperidine-3-carboxylic acid;
(3S)-1-[5-Methyl-6-(propan-2-yl)-2-[trans-4-(trifluoromethyl)cyclohexyl]pyrazolo[1,5-a]pyrimidin-7-yl]-3-(propan-2-yl) piperidine-3-carboxylic acid;
(3R)-1-[5-Methyl-6-(propan-2-yl)-2-[trans-4-(trifluoromethyl)cyclohexyl]pyrazolo [1,5-a]pyrimidin-7-yl]-3-propylpiperidine-3-carboxylic acid; and
(3S)-1-[5-Methyl-6-(propan-2-yl)-2-[trans-4-(trifluoromethyl)cyclohexyl]pyrazolo[1,5-a]pyrimidin-7-yl]-3-propylpiperidine-3-carboxylic acid.

22. A compound according to claim 5 selected from the group consisting of
(3R)-3-(Fluoromethyl)-1-[5-methyl-6-(propan-2-yl)-2-[trans-4-(trifluoromethyl) cyclohexyl]pyrazolo[1,5-a]pyrimidin-7-yl]piperidine-3-carboxylic acid;
(3R)-1-[5-Methyl-6-(propan-2-yl)-2-[trans-4-(trifluoromethyl)cyclohexyl]pyrazolo [1,5-a]pyrimidin-7-yl]piperidine-3-carboxylic acid;
(3S)-3-Methyl-1-[5-methyl-6-(propan-2-yl)-2-[trans-4-(trifluoromethyl)cyclohexyl]pyrazolo[1,5-a]pyrimidin-7-yl]piperidine-3-carboxylic acid; and
(3S)-3-Ethyl-1-[5-methyl-6-(propan-2-yl)-2-[trans-4-(trifluoromethyl)cyclohexyl]pyrazolo[1,5-a]pyrimidin-7-yl]piperidine-3-carboxylic acid.

23. A compound according to claim 5 selected from the group consisting of
(3R) -1-[5-Methyl-6-(propan-2-yl)-2-[trans-4-(trifluoromethyl)cyclohexyl]pyrazolo [1,5-a]pyrimidin-7-yl]-3-(propan-2-yl)piperidine-3-carboxylic acid;
(3S)-1-[3 -Fluoro-5-methyl-6-(propan-2-yl)-2-[trans-4-(trifluoromethyl)cyclohexyl]pyrazolo[1,5-a]pyrimidin-7-yl]-3-methylpiperidine-3-carboxylic acid;
(3S)-3-Ethyl-1-[3-fluoro-5-methyl-6-(propan-2-yl)-2-[trans-4-(trifluoromethyl) cyclohexyl]pyrazolo[1,5-a]pyrimidin-7-yl]piperidine-3-carboxylic acid; and
(3S)-1-{3-Fluoro-6-methoxy-5-methyl-2-[trans-4-(trifluoromethyl)cyclohexyl]pyrazolo[1,5-a]pyrimidin-7-yl}-3-methylpiperidine-3-carboxylic acid.

24. The method of claim 11, wherein the disorder is urinary incontinence.

* * * * *